US008735343B2

(12) United States Patent
White

(10) Patent No.: US 8,735,343 B2
(45) Date of Patent: *May 27, 2014

(54) PRODUCT AND PROCESS FOR LIQUEFACTION OF MUCUS OR SPUTUM

(71) Applicant: National Jewish Health, Denver, CO (US)

(72) Inventor: Carl W. White, Denver, CO (US)

(73) Assignee: National Jewish Health, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/644,099

(22) Filed: Oct. 3, 2012

(65) Prior Publication Data

US 2013/0209432 A1    Aug. 15, 2013

Related U.S. Application Data

(63) Continuation of application No. 12/464,753, filed on May 12, 2009, now abandoned, which is a continuation of application No. 11/681,587, filed on Mar. 2, 2007, now Pat. No. 7,534,438, which is a continuation of application No. 10/660,118, filed on Sep. 10, 2003, now Pat. No. 7,195,766.

(60) Provisional application No. 60/462,082, filed on Apr. 11, 2003, provisional application No. 60/409,960, filed on Sep. 10, 2002.

(51) Int. Cl.
*A61K 38/00* (2006.01)
*A61K 31/4535* (2006.01)
*C07K 14/00* (2006.01)

(52) U.S. Cl.
USPC ............. 514/1.8; 514/1.5; 530/324; 530/350; 424/185.1; 424/450

(58) Field of Classification Search
None
See application file for complete search history.

(56) References Cited

U.S. PATENT DOCUMENTS

| | | | |
|---|---|---|---|
| 3,091,569 A | 5/1963 | Sheffner | |
| 3,502,779 A | 3/1970 | Dye et al. | |
| 4,771,036 A | 9/1988 | Pigiet et al. | |
| 5,380,758 A | 1/1995 | Stamler et al. | |
| 5,908,611 A | 6/1999 | Gottlieb et al. | |
| 5,925,334 A | 7/1999 | Rubin et al. | |
| 5,985,261 A * | 11/1999 | White et al. | 424/85.1 |
| 6,303,642 B1 | 10/2001 | Susilo et al. | |
| 7,071,307 B2 * | 7/2006 | Dalmia et al. | 530/350 |
| 7,195,766 B2 * | 3/2007 | White | 424/185.1 |
| 7,534,438 B2 * | 5/2009 | White | 424/185.1 |
| 2005/0260140 A1 | 11/2005 | White et al. | |
| 2009/0311231 A1 | 12/2009 | White | |

FOREIGN PATENT DOCUMENTS

| | | |
|---|---|---|
| WO | WO 91/04320 | 4/1991 |
| WO | WO 02/078683 | 10/2002 |

OTHER PUBLICATIONS

Arner, E. et al., "Physiological functions of thioredoxin and thioredoxin reductase," Eur. J. Biochem., Oct. 2000, vol. 267(20), pp. 6102-6109.
Bell et al., "Role of the cystine-knot motif at the C-terminus of rat mucin protein Muc2 in dimer formation and secretion," Biochem J., Jul. 2001, vol. 357, pp. 203-209.
Brown et al. "Pulmonary dysfunction in cystic fibrosis is associated with oxidative stress," European Respiratory Journal, Feb. 1, 1996, vol. 9, No. 2, pp. 334-339.
Del Val, D. et al., Thioredoxin-(dithiol-)linked inactivation of elastase, Mol. Immunol., Jan. 2001, vol. 38, pp. 759-763.
Fuchs et al., "Effect of aerosolized recombinant human DNase on exacerbations of respiratory symptoms and on pulmonary function in patients with cystic fibrosis. The Pulmozyme Study Group," N. Engl J. Med., Sep. 1994, vol. 331(10), pp. 637-642.
Fuloria et al., "Evaluating the efficacy of mucoactive aerosol therapy," Respir Care, Jul. 2000, vol. 45(7), pp. 868-873.
Harper et al., "Activation of nuclear factor-kappa b transcriptional activity in airway epithelial cells by thioredoxin but not by N-acetyl-cysteine and glutathione," Am. J. Respir. Cell Mol. Biol., Aug. 2001, vol. 25, pp. 178-185.
Holmgren "Thioredoxin," Annual Reviews of Biochemistry, 1985, vol. 54, pp. 237-271.
Isowa et al. "Human Thioredoxin Attenuates Hypoxia-Reoxygenation Injury of Murine Endothelial Cells in a Thiol-Free Condition." Journal of Cellular Physiology, 2000, vol. 182, pp. 33-40.
Lamoureux et al., "Synthesis of Dithiols as Reducing Agents for Disulfides in Neutral Aqueous Solutions and Comparison of Reduction Potentials," J. Org. Chem., 1993, vol. 58, pp. 633-641.
Oblong et al., "Purification of human thioredoxin reductase: properties and characterization by absorption and circular dichroism spectroscopy," Biochemistry, Jul. 1993, vol. 32, pp. 7271-7277.
Rancourt, R. et al., "Thioredoxin liquefies and decreases the viscoelasticity of cystic fibrosis sputum," American Journal of Physiology, May 2004, vol. 286(5), pp. L931-L938.
Sun et al., "Additive effect of dornase alfa and Nacystelyn on transportability and viscoelasticity of cystic fibrosis sputum," Can Respir J., Nov.-Dec. 2002, vol. 9(6), pp. 401-406.

(Continued)

*Primary Examiner* — James H Alstrum Acevedo
*Assistant Examiner* — Li Lee
(74) *Attorney, Agent, or Firm* — Sheridan Ross P.C.

(57) ABSTRACT

Disclosed are compositions and methods for decreasing the viscosity and/or cohesiveness of and/or increasing the liquefaction of excessively or abnormally viscous or cohesive mucus or sputum. The composition contains a protein or peptide containing a thioredoxin active-site in reduced state and optionally further contains a reducing system.

17 Claims, 6 Drawing Sheets

(56) References Cited

OTHER PUBLICATIONS

Tabachnik et al., "Biochemical and rheological characterization of sputum mucins from a patient with cystic fibrosis," J. Biol. Chem., Jul. 1981, vol. 256(14), pp. 7161-7165.

Tang et al., "Thiol oxidation of actin produces dimers that enhance the elasticity of the F-actin network," Biophys. J., Apr. 1999, vol. 76, pp. 2208-2215.

Wang et al., "Oxidative stress disrupts glucocorticoid hormone-dependent transcription of the amiloride-sensitive epithelial sodium channel alpha-subunit in lung epithelial cells through ERK-dependent and thioredoxin-sensitive pathways," J. Biol. Chem., Mar. 2000, vol. 275(12), pp. 8600-8609.

International Search Report for International (PCT) Patent Application No. PCT/US03/28526, mailed Oct. 19, 2004.

Written Opinion for International (PCT) Patent Application No. PCT/US03/28526, mailed Dec. 28, 2004.

International Preliminary Examination Report for International (PCT) Patent Application No. PCT/US03/28526, mailed Mar. 29, 2008.

International Search Report for International (PCT) Patent Application No. PCT/US05/10061, mailed Feb. 22, 2006.

Written Opinion for International (PCT) Patent Application No. PCT/US05/10061, mailed Feb. 22, 2006.

International Preliminary Report on Patentability for International (PCT) Patent Application No. PCT/US05/10061, issued Sep. 26, 2006.

Examiner's First Report for Australian Patent Application No. 2003270561, dated Apr. 15, 2008.

Notice of Acceptance for Australian Patent Application No. 2003270561, dated Mar. 25, 2009.

Supplementary European Search Report for European Patent Application No. 03752262, issued on May 27, 2009.

\* cited by examiner

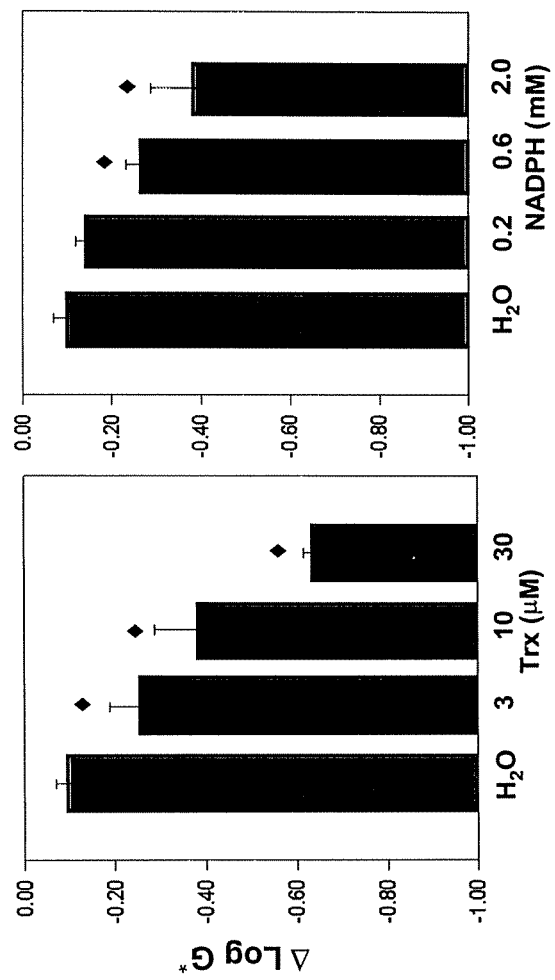

PRODUCT AND PROCESS FOR LIQUEFACTION OF MUCUS OR SPUTUM

CROSS-REFERENCE TO RELATED APPLICATIONS

This application is a Continuation of U.S. application Ser. No. 12/464,753, filed May 12, 2009, now abandoned, which is a Continuation of U.S. application Ser. No. 11/681,587, filed Mar. 2, 2007, now U.S. Pat. No. 7,534,438, which is a Continuation of U.S. application Ser. No. 10/660,118, filed Sep. 10, 2003, now U.S. Pat. No. 7,195,766, which claims the benefit of priority under 35 U.S.C. §119(e) from each of U.S. Provisional Application Ser. No. 60/409,960, filed Sep. 10, 2002 and U.S. Provisional Application Ser. No. 60/462,082, filed Apr. 11, 2003. The entire disclosure of each of U.S. application Ser. Nos. 11/681,587 and 10/660,118, and U.S. Provisional Application Ser. Nos. 60/409,960 and 60/462,082 is incorporated herein by reference.

REFERENCE TO A SEQUENCE LISTING

This application contains a Sequence Listing submitted electronically as a text file by ESF-Web. The text file, named "Seq_listing", has a size in bytes of 14 KB, and was recorded on Feb. 12, 2004. The information contained in the text file is incorporated herein by reference in its entirety pursuant to 37 § CFR 1.52(e)(5).

FIELD OF THE INVENTION

This invention generally relates to the use of a protein or peptide containing a thioredoxin active-site in reduced state to induce, enhance and/or increase the liquefaction of mucus or sputum.

BACKGROUND OF THE INVENTION

Cystic fibrosis (CF) is a common lethal genetic disease that results from a mutation in the gene encoding a chloride channel protein, the CF transmembrane conductance regulator. As a result of this defect, epithelia within the body are impermeable to chloride ion transport (Boucher et al., *Lung* 161:1-17, 1983; Welsh, *Physiol Rev* 67:11443-1184, 1987). Although several organs are affected, including pancreas, intestine, and male genital tract, complications within the lung account for 95% of the morbidity and mortality (Means, M. Cystic Fibrosis: the first 50 years. In: *Cystic Fibrosis—Current Topics* Volume 1, edited by Dodge J A, Brock D J H, and Widdicombe J H. Chichester: Wiley and Sons, 1992, p. 217-250). In lung impaired by the disease, chloride transport into the airway lumen leads to excessive absorption of $Na^+$ and fluid, reducing the volume of airway surface liquid (Jiang et al., *Science* 262:424-427, 1993). Desiccation of airway surface liquid leads to the concentration of mucin macromolecules, which are the gel forming constituents of mucus (Matsui et al., *Cell* 95:1005-1015, 1998). The viscoelastic properties of normal mucus are dependent on the concentration, molecular weight, and entanglements between mucin polymers (Verdugo et al., *Biorheology* 20:223-230, 1983). Further interaction of mucins with DNA (Potter et al., *Am J Dis Child* 100:493-495, 1960; Lethem et al., *Am Rev Respir Dis* 100:493-495, 1990; Lethem et al., *Eur Respir J* 3:19-23, 1990) and f-actin polymers (Sheils et al., *Am J Path* 148:919-927, 1996; Tomkiewicz et al., DNA and actin filament ultrastructure in cystic fibrosis sputum. In: *Cilia, mucus, and mucociliary interactions*, edited by Baum G L, Priel Z, Roth Y, Liron N, and Ostfeld E J. New York, N.Y.: Marcel Dekker, 1998) released from dying inflammatory cells is responsible for the dense and viscous nature of CF sputum. The inability to clear such mucus by cough or mucociliary clearance facilitates colonization of the lung with opportunistic pathogens.

While the etiology of CF lung disease can be attributed to the altered rheological properties of sputum, compromised lung function is rarely evident at birth. Instead, bronchiectasis and airway obstruction progress with age of patient. This chronic lung injury results from a persistent cycle of bacterial infection and inflammatory response. Airway damage results when neutrophils recruited into the lung release matrix degrading enzymes, such as elastase, and harmful reactive oxygen species (reviewed in Konstan and Berger, *Pediatr Pulmonol* 24:137-142, 1997).

Despite some promising advances, correction of CF by gene therapy is not yet attainable. Currently, antibiotic regimens coupled with drugs that facilitate the clearance of purulent airway secretions remain the mainstay treatments for progressive airway disease Inhalation of purified rhDNase (Pulmozyme; Genentech, USA), which digests extracellular DNA present in the CF airway, is widely used as a respiratory decongestant. Such treatment is clinically effective for diminishing sputum viscosity and stabilizing the forced expiratory volume (FEV) (Fuchs et al., *N Engl J Med* 331:637-642, 1994). Other investigative therapies aimed at breaking down mucin or actin polymers, including N-acetylcysteine, nacystelyn (an N-acetyl-L-cysteine derivative), and gelsolin, can also reduce sputum viscosity experimentally, but have yet to attain clinical approval specifically for treatment of CF in the United States.

Therefore, there is a need in the art for improved therapeutic approaches for the treatment of cystic fibrosis, as well as other diseases and conditions that are associated with abnormally or excessively viscous or cohesive mucus or sputum.

SUMMARY OF THE INVENTION

One embodiment of the present invention relates to a method to increase the liquefaction of mucus or sputum in a patient that has excessively viscous or cohesive mucus or sputum. The method includes the step of contacting the mucus or sputum of the patient with a composition comprising a protein or peptide containing a thioredoxin active-site in reduced state effective to increase the liquefaction of the mucus or sputum as compared to prior to the step of contacting. In one aspect of this embodiment, the patient has a lung disease in which abnormal or excessive viscosity or cohesiveness of mucus or sputum is a symptom or cause of the disease including, but not limited to, cystic fibrosis.

In one aspect, the step of contacting the mucus or sputum of the patient with the composition is performed by introducing the composition to the patient by a route selected from the group consisting of nasal, intratracheal, bronchial, direct installation into the lung and inhaled. In one aspect, the mucus or sputum to be contacted is located in the respiratory tract, the gastrointestinal tract or the reproductive tract of the patient. In another aspect, the composition is administered to the patient in a pharmaceutically acceptable carrier. Preferably, a liquid phase of a total volume of a sample of mucus or sputum from the patient shows a statistically significant increase after administration of the composition.

In one aspect of this embodiment, the protein or peptide is administered to the patient in an amount that is between about 1.5 mmoles/kg weight of the patient and about 150 mmoles/kg weight of the patient. In another aspect, the protein has a half-life in the patient of between about 5 minutes and about 24 hours. In one aspect, the thioredoxin active-site comprises the amino acid sequence C-X-X-C, wherein C residues are in reduced state, and wherein X residues are any amino acid residue. In another aspect, the thioredoxin active-site comprises the amino acid sequence X-C-X-X-C-X, wherein C residues are in reduced state, and wherein X residues are any amino acid residue. In another aspect, the thioredoxin active-site comprises the amino acid sequence X-C-G-P-C-X (SEQ ID NO:2), wherein C residues are in reduced state, and wherein X residues are any amino acid residue. In yet another aspect, the thioredoxin active-site comprises the amino acid sequence W-C-G-P-C-K (SEQ ID NO:3), wherein C residues are in reduced state. In another aspect, the protein comprises thioredoxin selected from the group consisting of prokaryotic thioredoxin, yeast thioredoxin, plant thioredoxin, and mammalian thioredoxin. In a preferred aspect, the protein comprises human thioredoxin.

In one aspect of the invention, the composition further comprises nicotinamide-adenine dinucleotide phosphate (reduced form) (NADPH) for reducing the thioredoxin active site of the protein. In a further aspect, the composition comprises thioredoxin reductase.

Yet another embodiment of the invention relates to a composition for use in the liquefaction of mucus or sputum, comprising a protein or peptide containing a thioredoxin active-site in reduced state and at least one additional agent for treatment of excessively viscous or cohesive mucus or sputum. In one aspect, the thioredoxin active-site comprises the amino acid sequence X-C-X-X-C-X, wherein C residues are in reduced state, and wherein the X residues are any amino acid residue. In another aspect, the thioredoxin active-site comprises the amino acid sequence X-C-G-P-C-X (SEQ ID NO:2), wherein C residues are in reduced state, and wherein the X residues are any amino acid residue. In yet another aspect, the thioredoxin active-site comprises the amino acid sequence W-C-G-P-C-K (SEQ ID NO:3), wherein C residues are in reduced state. In yet another aspect, the protein comprises thioredoxin selected from a group consisting of prokaryotic thioredoxin, yeast thioredoxin, plant thioredoxin, and mammalian thioredoxin. In one aspect, the protein comprises human thioredoxin.

The composition can, in a further aspect, include nicotinamide-adenine dinucleotide phosphate (reduced form) (NADPH). In a further aspect, the composition further comprises thioredoxin reductase.

Yet another embodiment of the present invention relates to a method to increase the liquefaction of mucus or sputum in a patient that has excessively viscous or cohesive mucus or sputum. The method includes the step of contacting the mucus or sputum in the respiratory tract of the patient with a composition comprising a protein comprising the amino acid sequence X-C-X-X-C-X, wherein C residues are in reduced state, wherein the contact of composition increases the volume of the liquid phase in a sample of mucus or sputum from the patient as compared to prior to contact with the composition.

BRIEF DESCRIPTION OF THE DRAWINGS OF THE INVENTION

FIG. 4A shows the effect of Trx dose on viscoelasticity (log G*) of CF sputum in vitro.

FIG. 4B shows the effect of NADPH dose on viscoelasticity (log G*) of CF sputum in vitro.

DETAILED DESCRIPTION OF THE INVENTION

Figure 1A:
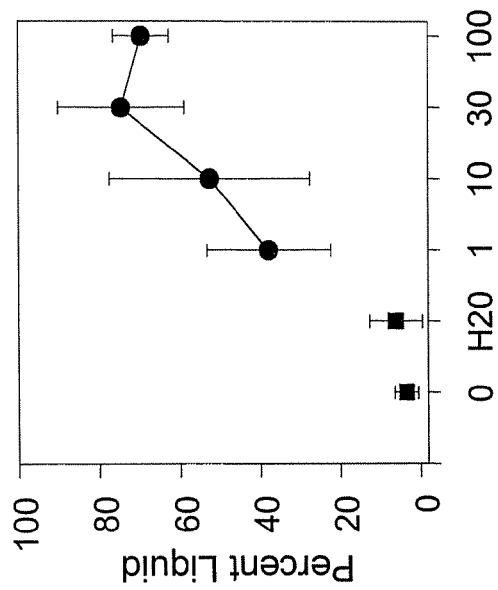
FIG. 1A is a line graph showing that liquefaction of CF sputum by exposure to the Trx reducing system is dose-dependent.

The present invention generally relates to the use of a protein or peptide containing a thioredoxin active-site in reduced state to induce, enhance and/or increase the liquefaction of mucus or sputum. More specifically, the present inventor has discovered that thioredoxin can decrease the viscosity and/or cohesivity of sputum or mucus and thereby is an effective agent for the liquefaction of sputum or mucus. Accordingly, native thioredoxin, proteins or peptides containing the active-site of thioredoxin in reduced state, or nucleic acid molecules encoding such proteins, can be used alone or in a composition to treat a variety of conditions or diseases associated with undesirable mucus or tenacious and viscous sputum. For example, respiratory diseases such as cystic fibrosis are particularly amenable to treatment using the product and process of the invention. Therefore, the present invention relates to the use of proteins containing the active-site of thioredoxin in reduced state for the increased liquefaction of mucus or sputum, particularly mucus or sputum that is abnormally or excessively viscous and/or cohesive. The proteins are administered to a patient that is suffering from or affected by such abnormal or excessive mucus or sputum in a manner and amount effective to increase the liquefaction of the mucus or sputum and preferably, to provide a therapeutic benefit to the patient.

Thioredoxin and proteins containing the thioredoxin active site have advantages over other reducing agents for use in the treatment of conditions such as cystic fibrosis. For example, unlike other reducing agents (e.g., N-acetylcysteine (NAC), Nacystelyn (NAL), dithiothreitol (DTT)), thioredoxin can be cyclically re-reduced to its effective (reduced) form. In addition, auto-oxidation (e.g., producing superoxide, hydrogen peroxide, hydroxyl radical and other toxic oxygen metabolites) of thioredoxin occurs at a low level as compared with other reducing agents such as NAC, NAL and DTT. Furthermore, thioredoxin is a naturally occurring compound which normally exists in the extracellular space, and therefore, introduction of thioredoxin into the airway should not induce an immune response and should be non-irritating. Thioredoxin is also not glycosylated, and as such, administration of the protein in natural or recombinant form should not induce an innate immune response. Perhaps even more significantly, thioredoxin, in contrast to other reducing agents, maintains the treated mucus or sputum in the liquid state. NAC and DTT, for example, become "spent" or oxidized over time and at this stage, liquified sputum or mucus can revert back to the more viscous "gel" state. In contrast, the liquefaction produced by thioredoxin appears to endure for hours, most likely due to its cyclic re-reduction by its reducing system. Finally, thioredoxin is more potent than other reducing agents and therefore, it can be used at significantly lower doses than other agents to achieve a beneficial effect.

In addition to the above-described advantages, thioredoxin has other benefits which increase its usefulness in disease conditions. For example, it is known that thioredoxin induces MnSOD (e.g., see U.S. Pat. No. 5,985,261 to White et al., incorporated herein by reference in its entirety) which is predicted to decrease the toxicity of certain bacterial toxins (including, but not limited to, endotoxin from bacterial cell walls of gram-negative bacteria, pyocyanin from *Pseudomonas aeruginosa*, and others) in disease sputum (e.g., cystic fibrosis sputum). In addition, thioredoxin has anti-inflammatory properties which can enhance the overall treatment of a respiratory condition.

Thioredoxin (Trx) is a protein disulfide reductase that catalyzes numerous thiol-dependent cellular reductive processes. Thioredoxin (Trx) contains two redox-active cysteines which are highly conserved across species. In their oxidized form, these cysteines form a disulfide bridge that protrudes from the three dimensional structure of the protein (Holmgren, *Annu Rev Biochem* 54:237-271, 1985). Reduction of this active center by the NADPH-dependent thioredoxin reductase (TR) enzyme allows Trx to function as an electron carrier with dithiol/disulfide exchange capability (Oblong et al., *Biochemistry* 32:7271-7277, 1993). Protein disulfides are a preferred substrate for Trx-mediated reducing action. The persistent and viscous nature of airway secretions in cystic fibrosis disease leads to airway obstruction, opportunistic infection, and deterioration of lung function. Recognizing that respiratory mucins contain several cysteine domains that are believed to play an essential role in polymerization (Bell et al., *Biochem J* 357:203-209, 2001; Asker et al., *Biochem J* 333:381-387, 1998), the present inventor sought to determine whether Trx could serve as an effective mucolytic by reduction of mucin disulfides.

In the experiments discussed herein, the present inventor examined the effects of the Trx reducing system (thioredoxin, thioredoxin reductase, and NADPH) on the physical and rheologic properties of CF sputum in vitro. Sputum obtained from CF patients was treated with TRX and its reducing system [0.1 µM Thioredoxin reductase (TR)+2 mM NADPH] and liquid phase:gel phase ratio (percent liquid phase) assessed by compaction assay. Exposure to low Trx concentrations (1 µM) caused significant increases in the percentage of liquid phase of sputum. Maximal increases in percent liquid phase occurred with 30 µM Trx. Additional measurements revealed that sputum liquefaction by the Trx reducing system is dependent on NADPH concentration. The relative potency of the Trx reducing system also was compared with other disulfide reducing agents. In contrast with Trx, glutathione and N-acetylcysteine were ineffective in liquefying sputum when used at concentrations below 1 mM. Sputum viscoelasticity, measured by magnetic microrheometry, was also significantly diminished following 20 minute treatment with 3, 10, or 30 µM Trx. Similarly, this reduction in viscoelasticity was also dependent upon NADPH concentration. Further experimentation has indicated that Trx treatment increases the solubility of high molecular weight glycoproteins, and causes redistribution of extracellular DNA into the liquid phase of sputum. The experiments described herein demonstrate that in vitro treatment with catalytic amounts of Trx and its reducing system can liquefy and decrease the viscoelasticity of purulent CF sputum. The increased solubility of high molecular weight glycoproteins present in Trx-treated sputum indicates that mucin macromolecules may be the substrates reduced by Trx during the mucolytic process.

Mucus obstruction of the airways can cause significant morbidity and mortality in patients with CF. The present inventor has demonstrated that the viscoelastic properties facilitating the persistence of these secretions within airways are markedly diminished by Trx. This conclusion is supported by two lines of experimental evidence. First, compaction assay results indicate that large amounts of liquid are released from the gel matrix of CF sputum during incubation with Trx. Occurring simultaneously with this release were decreases in the volume of solid matter, indicating that the gel forming constituents of sputum were being solubilized. This liquefaction of CF sputum could often be observed grossly in CF sputum samples during the incubation period, and therefore, is not an artifact of centrifugal disruption. The liberation of liquid by Trx is expected to have important therapeutic implications since restoration of water volume at airway surfaces can restore the mucociliary transport ability of CF epithelium (Jiang et al., *Science* 262:424-427, 1993). Second, magnetic microrheometry measurements provide direct evidence that sputum viscoelasticity declines as a result of reduction of sputum components by Trx.

CF sputum is a non-newtonian fluid exhibiting both liquid and solid characteristics. Polymers when present in solutions at low concentration are able to rotate freely. When polymers become concentrated or cross-linked to such a degree that their rotation is hindered, a solution has reached a transition phase called the percolation threshold (Forgacs, *J Cell Sci* 108:2131-2143, 1995). At the percolation threshold the solution begins to acquire characteristics of a solid, and the elastic moduli continue to increase as more cross-polymer interactions are added, until each filament in the sample is incorporated into the matrix. Biochemical analyses have revealed that mucins MUC5AC and MUC5B, secreted by cells lining the respiratory tract, are the major gel forming polymers components of airway mucus (Hovenberg et al., *Glycoconj J* 13:839-847, 1996; Thornton et al., *Biochem J* 316:967-975, 1996; Thornton et al., *J Biol Chem* 272:9561-9566, 1997). Cysteine domains present on these mucins contribute to polymer formation, and possibly interaction with neighboring mucin chains, by disulfide bond formation (Bell et al., *Biochem J* 357:203-209, 2001; Asker et al., *Biochem J* 333:381-387, 1998). Since disulfide bonds on proteins are the preferred substrates for Trx enzymatic activity, it was hypothesized by the inventor that mucin polymers were targets for reduction during the liquefaction of sputum by Trx. This hypothesis was supported by PAS staining which revealed changes in the solubility of high molecular weight glycoforms in Trx treated sputum. Detection of greater concentrations of glycoproteins in the liquid phase of Trx-exposed sputum was further indicated by a more intense yellow color and had greater opacity than liquid phase derived from diluent-treated samples. The enhanced electrophoretic mobility of PAS-detectable glycoproteins in Trx-exposed sputum also suggests that these macromolecules may decrease in size during enzymatic reduction. Findings from this electrophoretic analysis are in agreement with compaction assay measurements by demonstrating that glycoprotein release into liquid phase coincides with the decrease in mass of the gel matrix during exposure to Trx.

Neutrophil lysis within the airways of diseased CF lungs results in the deposition of extracellular DNA into airway secretions (Lethem et al., *Eur Respir J* 3:19-23, 1990). By non-covalent interactions, this DNA becomes entangled within mucin glycoproteins, increasing mucus gel viscoelasticity (Sachdev et al., *Chest* 81:41 S-43S, 1982). In the experiments described herein, the present inventor found that DNA present in sputum becomes increasingly soluble following Trx treatment. A logical explanation is that Trx activity causes structural changes within the gel matrix which are sufficient to relieve entanglement interactions between DNA and the affected macromolecules. It is uncertain what the relative contribution of this increased DNA solubility has toward viscoelastic changes observed during exposure of CF sputum to Trx. Nonetheless, from a clinical standpoint, removal of DNA from the insoluble gel phase of sputum could render it more susceptible to DNase activity during such treatment in CF. Therefore, the method of the invention has a strong potential for synergy with other existing "state of the art" therapies for CF.

Figure 2:
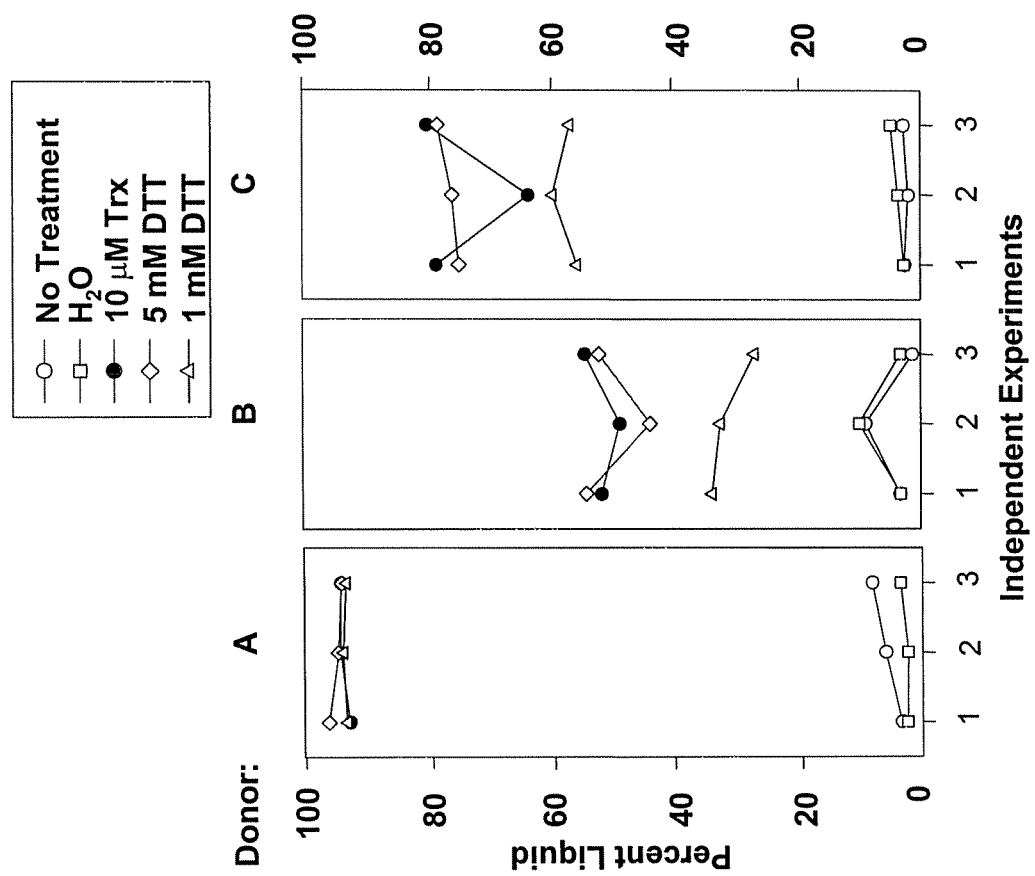
FIG. 2 is a line graph showing an assessment of compaction assay reproducibility.

In studies comparing the sputum liquefying abilities of other thiol reducing agents, Trx demonstrated greater efficacy than the glutathione (GSH; reduced glutathione) reducing system. Since Trx has two redox active cysteine residues (dithiol), whereas GSH contains only one (monthiol), Trx may be more efficient in reduction of disulfide bonds in the gel-forming constituents of CF sputum. With regard to non-recycling mucolytic drugs, DTT was more effective on an equimolar basis than NAC (or MUCOMYST®) solutions (FIGS. 2 and 3; and data not shown). Efficacy of these compounds may again be dependent on the number of redox active cysteine residues, DTT having two, NAC only one. On the basis of these compaction assay measurements, enzymatic disulfide bond reduction using proteins, peptides or other compounds with dual redox active cysteines is expected to be a potent mucolytic strategy.

In summary, Trx increases the liquid fraction and diminishes the viscoelasticity of CF sputum. Increases in glycoprotein solubility occur during treatment of sputum with Trx, and this may be the mechanism for these rheological changes. The development of mucus reducing systems that stimulate release of liquid, and reduce the viscosity of airway secretions, is expected to have therapeutic potential for CF, as well as for the treatment of excessive or abnormal mucus viscosity and/or cohesiveness that may be associated with other respiratory conditions (e.g., chronic or acute bronchitis; bronchiectasis; acute tracheitis; acute or chronic sinusitis; atelectasis resulting from acute or chronic mucus plugging of the airways; bronchiolitis) or with various gastrointestinal or reproductive disorders associated with or exacerbated by excessive or abnormal mucus viscosity and/or cohesiveness (e.g., acute, subacute or chronic bowel obstruction due to mucus inspissation; infertility due to obstruction of vital reproductive structures). Since Trx is a native protein which lacks glycosylation and post-translational modification, and normally appears at low level within extracellular space, its chronic administration could be tolerated well by the immune system.

Accordingly, one embodiment of the present invention relates to a method to increase the liquefaction of mucus or sputum in a patient that has excessively viscous or cohesive mucus or sputum. The method includes the step of contacting the mucus or sputum of the patient with a composition comprising a protein or peptide containing a thioredoxin active-site in reduced state. The protein is effective to increase the liquefaction of the mucus or sputum as compared to prior to the step of contacting.

According to the present invention, the term "mucus" generally refers to a usually clear viscid fluid that is secreted by mucous membranes in various tissues of the body, including by the respiratory, gastrointestinal, and reproductive tracts. Mucus moistens, lubricates and protects the tissues from which it is secreted. It comprises mucin macromolecules, which are the gel forming constituents of mucus. The viscoelastic properties of normal mucus are dependent on the concentration, molecular weight, and entanglements between mucin polymers. The term "sputum" generally refers to a mixture of saliva and discharge from the respiratory passages, including mucus. Sputum is typically an expectorated mixture of saliva and mucus (and other discharge from the respiratory tissues). Therefore, mucus is a primary component of sputum, and as such, the presence of excessively viscous mucus in sputum results in a sputum which is itself excessively viscous. The term "liquefaction" refers to the act of becoming liquid. Therefore, an increase in the liquefaction of mucus or sputum refers to the increase in liquid phase or liquid state of mucus or sputum, as compared to a more solid or viscous phase.

The general functions of mucus and sputum in the body require that the mucus (and thus the mucus component of the sputum) have viscoelastic properties. In an individual with normal mucus and sputum (i.e., a healthy individual, or more particularly, an individual who does not suffer from symptoms or a condition caused or exacerbated by the viscosity or cohesiveness of mucus or sputum), the viscoelasticity is dependent on the concentration, molecular weight, and entanglements between mucin polymers (Verdugo et al., *Biorheology* 20:223-230, 1983). When mucins in the mucus interact with DNA (Potter et al., *Am J Dis Child* 100:493-495, 1960; Lethem et al., *Am Rev Respir Dis* 100:493-495, 1990; Lethem et al., *Eur Respir J* 3:19-23, 1990) and f-actin polymers (Sheils et al., *Am J Path* 148:919-927, 1996; Tomkiewicz et al., DNA and actin filament ultrastructure in cystic fibrosis sputum. In: Cilia, mucus, and mucociliary interactions, edited by Baum G L, Priel Z, Roth Y, Liron N, and Ostfeld E J. New York, N.Y.: Marcel Dekker, 1998) released from dying inflammatory cells, the mucus (and thus sputum) becomes much more dense and viscous, such as in CF sputum. The inability to clear such mucus by cough or mucociliary clearance facilitates colonization of the lung with opportunistic pathogens. Therefore, abnormally or excessively viscous and/or cohesive mucus is characterized as mucus that is measurably or detectably more viscous or cohesive than mucus from a normal or healthy patient (preferably an age and sex-matched patient), and/or as mucus which, by virtue of its level of viscosity and/or cohesiveness, causes or contributes to at least one symptom in a patient that causes discomfort or pain to the patient, or that causes or exacerbates a condition or disease. In other words, abnormally or excessively viscous and/or cohesive sputum is a deviation from normal mucus or sputum wherein it is desirable to treat the patient to provide some relief from the condition or other therapeutic benefit.

The method and composition of the present invention can be used to treat any patient in which it is desirable to increase the liquefaction of mucus or sputum. In particular, patients that have certain lung, sinus, nasal, gastrointestinal, or reproductive diseases or conditions can benefit from treatment using the method of the present invention. The present invention is most useful for ameliorating or reducing at least one symptom of a condition or disease that is caused by or exacerbated by abnormal or excessive viscosity and/or cohesiveness of the mucus or sputum, which of course can include the lung-associated disease, cystic fibrosis. Other diseases may, at least some of the time, be associated with abnormal or excessive viscosity and/or cohesiveness of the mucus or sputum, and when such a symptom occurs, the method of the present invention can be used to increase liquefaction of the mucus or sputum and provide at least some relief or therapeutic benefit to the patient. Examples of such diseases include, but are not limited to: cystic fibrosis; chronic or acute bronchitis; bronchiectasis (non-CF and CF bronchiectasis);

acute tracheitis (bacterial, viral, mycoplasmal or caused by other organisms); acute or chronic sinusitis; atelectasis (lung or lobar collapse) resulting from acute or chronic mucus plugging of the airways (sometimes seen in a variety of diseases such as asthma); bronchiolitis (viral or other); acute, subacute or chronic bowel obstruction due to mucus inspissation including, but not limited to meconium ileus or meconium ileus equivalent in CF or similar disorders; and infertility due to obstruction of (but not limited to) the cervix, seminal ducts or other vital reproductive structures. In addition, the composition and method of the present invention may be useful for reducing symptoms associated with excessive viscosity and/or cohesiveness of the mucus or sputum in patients with a variety of respiratory infections, including both viral and bacterial infections.

As such, a therapeutic benefit is not necessarily a cure for a particular disease or condition, but rather, preferably encompasses a result which most typically includes alleviation of the disease or condition, elimination of the disease or condition, reduction or elimination of a symptom associated with the disease or condition, prevention or alleviation of a secondary disease or condition resulting from the occurrence of a primary disease or condition (e.g., infectious disease caused by opportunistic pathogenic microorganisms that take advantage of the excessively viscous mucus in the respiratory tract), and/or prevention of the disease or condition, or a symptom associated with the disease or condition. As used herein, the phrase "protected from a disease" refers to reducing the symptoms of the disease; palliative therapy (relieving or soothing a symptom of the disease without effecting a cure); reducing the occurrence of the disease, and/or reducing the severity of the disease. Protecting a patient can refer to the ability of a composition of the present invention, when administered to a patient, to prevent a disease from occurring and/or to cure or to alleviate disease at least one symptom, sign or cause of the disease or condition. As such, to protect a patient from a disease includes both preventing disease occurrence (prophylactic treatment) and treating a patient that has a disease (therapeutic treatment). In particular, protecting a patient from a disease is accomplished by increasing the liquefaction of mucus or sputum in the patient by contacting the mucus or sputum with a protein or peptide comprising a thioredoxin active site in reduced state such that a beneficial effect is obtained. A beneficial effect can easily be assessed by one of ordinary skill in the art and/or by a trained clinician who is treating the patient. The term "disease" refers to any deviation from the normal health of a patient and includes a state when disease symptoms are present, as well as conditions in which a deviation (e.g., infection, gene mutation, genetic defect, etc.) has occurred, but symptoms are not yet manifested.

Contact of the mucus and/or sputum of a patient with the protein or peptide comprising a thioredoxin active site in reduced state (or composition comprising such a protein) is intended to result in increased liquefaction of the mucus or sputum as compared to prior to contact with the composition. According to the present invention, an increase in liquefaction of mucus or sputum can be any measurable or detectable increase in the level of liquefaction of mucus or sputum as compared to a prior level of liquefaction, and is preferably a statistically significant increase (i.e., differences in measured level of liquefaction between the patient sample and a baseline control are statistically significant with a degree of confidence of at least p<0.05). Typically, the "baseline control" is a patient sample prior to the administration of the treatment, since normal, healthy individuals generally cannot produce a quantity of sputum sufficient to serve as a control, although sputum from a normal, healthy individual is not excluded as a baseline control. Liquefaction of mucus or sputum can be measured using any suitable technique known in the art, including, but not limited to, compaction assays as described in the Examples section. In such an assay, the amount of mucus or sputum in a solid phase (gel) versus aqueous phase (liquid) is measured. In other aspects of the invention, the relative viscosity or cohesiveness of mucus or sputum can be measured using other parameters or indicators including, but not limited to, viscoelasticity (measured, for example, by magnetic microrheometry), glycoprotein content, or DNA content. In one aspect of the invention, the level of liquefaction is described as the amount of a given mucus or sputum sample that is in an aqueous (liquid) phase as a percentage of the total volume of the mucus or sputum sample. In a patient with cystic fibrosis, for example, the level of liquefaction of mucus or sputum can be as low as less than 10% or even less than 5% of the total volume. Preferably, contact of a protein or composition of the invention with the mucus or sputum results in a change in the liquefaction of the mucus or sputum of at least about such that at least about 15% of the total volume is in liquid phase, and more preferably, at least about 20% of the total volume is in liquid phase, and more preferably, at least about 25% of the total volume is in liquid phase, and more preferably, at least about 30% of the total volume is in liquid phase, and more preferably, at least about 35% of the total volume is in liquid phase, and more preferably, at least about 40% of the total volume is in liquid phase, and more preferably, at least about 45% of the total volume is in liquid phase, and more preferably, at least about 50% of the total volume is in liquid phase or until the blockage or inhibition of function caused by the mucus has cleared (e.g., until the patient airways are cleared sufficiently to begin expectorating the fluid). In general, it is preferred that the liquefaction of the sputum or mucus in increased in small, gradual increments until the airway or other blocked passage (e.g., in the gastrointestinal or reproductive tract) is cleared, but without excessively liquefying the sputum. Excessive liquefaction of the mucus or sputum is not desired, as it can be detrimental to the patient (e.g., liquefied sputum could flow backward and flood the small airways with an infected thin liquid before the sputum can be cleared by the patient). Preferably, the contact of a protein, peptide or composition of the invention with mucus or sputum produces at least about a 1% increase in the liquefaction of the mucus or sputum by volume as compared to prior to the treatment, more preferably, at least about a 2% increase, and so on, in increments of 1%, until the patient airways or other clogged passages are cleared.

In one aspect, the therapy is conducted in conjunction with methods to clear the thinned material from the affected tissue (respiratory tract, gastrointestinal tract, reproductive tract) of the patient. For example, in the case of the respiratory system, one can use the method of the present invention in conjunction with postural drainage, huff coughing and other respiratory exercises, or any other suitable method for expectorating the liquefied mucus or sputum.

According to the present invention, the mucus or sputum in the patient to be treated is contacted with a protein (or composition comprising the protein) that contains a thioredoxin active-site in reduced state. The protein is effective to reduce the viscosity and cohesivity of sputum or mucus and/or to increase the liquefaction of sputum or mucus as compared to prior to the step of contacting. As described previously, thioredoxin is a protein disulfide reductase found in most organisms which participates in many thiol-dependent cellular reductive processes. In humans, thioredoxin is also referred to as adult T cell leukemia-derived factor (ADF).

Intracellularly, most of this ubiquitous low molecular weight (11,700) protein remains reduced. Reduced or oxidized thioredoxin may be able to enter intact cells or absorb to the cell membrane, where a small amount is gradually internalized over time. It has two vicinal cysteine residues at the active-site which in the oxidized protein form a disulfide bridge located in a protrusion from the protein's three dimensional structure. The flavoprotein thioredoxin reductase catalyzes the NADPH-dependent reduction of this disulfide. Small increases in thioredoxin can cause profound changes in sulfhydryl-disulfide redox status in proteins.

In addition to its ability to effect the reduction of cellular proteins, it is recognized that thioredoxin can act directly as an antioxidant (e.g. by preventing oxidation of an oxidizable substrate by scavenging reactive oxygen species) although, unlike other thiols, thioredoxin does not generally contribute to the oxidative stress in a cell by autooxidizing (e.g. generating superoxide radicals through autooxidation). U.S. Pat. No. 5,985,261 to White et al., supra, showed that thioredoxin directly induces the production of MnSOD and that such induction is effected by thioredoxin in reduced state.

A "thioredoxin active-site" of the present invention comprises the amino acid sequence C-X-X-C. As used herein, amino acid residues denoted "C" are cysteine residues and amino acid residues denoted "X" can be any amino acid residue, and in particular, any of the standard 20 amino acid residues. Such a thioredoxin active-site of the present invention preferably comprises the amino acid sequence C-G-P-C (SEQ ID NO:1). A thioredoxin active-site can further comprise the amino acid sequence X-C-X-X-C-X. Preferably, a thioredoxin active-site of the present invention comprises the amino acid sequence X-C-G-P-C-X (SEQ ID NO:2), wherein such amino acid residue denoted "G" is a glycine residue, and wherein such amino acid residue denoted "P" is a proline residue. More preferably, a thioredoxin active-site of the present invention comprises the amino acid sequence W-C-G-P-C-K (SEQ ID NO:3), wherein such amino acid residue denoted "W" is a tryptophan residue, and wherein such amino acid residue denoted "K" is a lysine residue.

In one aspect of the invention, the protein containing an thioredoxin active site is a full-length thioredoxin protein or any fragment thereof containing a thioredoxin active site as described structurally and functionally above. Preferred thioredoxin proteins include prokaryotic thioredoxin, yeast thioredoxin, plant thioredoxin, and mammalian thioredoxin, with human thioredoxin being particularly preferred. The nucleic acid and amino acid sequences of thioredoxins from a variety of organisms are well known in the art and are intended to be encompassed by the present invention. For example, SEQ ID NOs:4-15 represent the amino acid sequences for thioredoxin from *Pseudomonas syringae* (SEQ ID NO:4), *Porphyromonas gingivalis* (SEQ ID NO:5), *Listeria monocytogenes* (SEQ ID NO:6), *Saccharomyces cerevisiae* (SEQ ID NO:7), *Gallus gallus* (SEQ ID NO:8), *Mus musculus* (SEQ ID NO:9), *Rattus norvegicus* (SEQ ID NO:10), *Bos taurus* (SEQ ID NO:11), *Homo sapiens* (SEQ ID NO:12), *Arabidopsis thaliana* (SEQ ID NO:13), *Zea mays* (SEQ ID NO:14), and *Oryza sativa* (SEQ ID NO:15). Referring to each of these sequences, the X-C-G-P-C-X (SEQ ID NO:2) motif (which includes the CGPC motif of SEQ ID NO:1) can be found as follows: SEQ ID NO:4 (positions 33-38), SEQ ID NO:5 (positions 28-33), SEQ ID NO:6 (positions 27-32), SEQ ID NO:7 (positions 29-34), SEQ ID NO:8 (positions 31-36), SEQ ID NO:9 (positions 31-36), SEQ ID NO:10 (positions 31-36), SEQ ID NO:11 (positions 31-36), SEQ ID NO:12 (positions 31-36), SEQ ID NO:13 (positions 59-64), SEQ ID NO:14 (positions 88-93) and SEQ ID NO:15 (positions 94-99). Moreover, the three-dimensional structure of several thioredoxin proteins has been resolved, including human and bacterial thioredoxins. Therefore, the structure and active site of thioredoxins from multiple organisms is well known in the art and one of skill in the art would be able to readily identify and produce fragments or homologues of full length thioredoxins that can be used in the present invention.

The phrase "in reduced state" specifically describes the state of the cysteine residues in the active-site of a protein or peptide of the present invention. In reduced state, such cysteine residues form a dithiol (i.e. two free sulfhydryl groups, —SH). In contrast, in oxidized form, such cysteine residues form an intramolecular disulfide bridge; such a molecule can be referred to as cystine. In reduced state, a thioredoxin active-site is capable of participating in redox reactions through the reversible oxidation of its active-site dithiol to a disulfide, and catalyzes dithiol-disulfide exchange reactions.

As used herein, a protein of the present invention containing a thioredoxin active site can be a thioredoxin active site per se or a thioredoxin active site joined to other amino acids by glycosidic linkages. Thus, the minimal size of a protein or peptide of the present invention is from about 4 to about 6 amino acids in length, with preferred sizes depending on whether a full-length, fusion, multivalent, or merely functional portions of such a protein is desired. Preferably, the length of a protein or peptide of the present invention extends from about 4 to about 100 amino acid residues or more, with peptides of any interim length, in whole integers (i.e., 4, 5, 6, 7 . . . 99, 100, 101 . . . ), being specifically envisioned. In a further preferred embodiment, a protein of the present invention can be a full-length protein or any homologue of such a protein. As used herein, the term "homologue" is used to refer to a protein or peptide which differs from a naturally occurring protein or peptide (i.e., the "prototype" or "wild-type" protein) by modifications to the naturally occurring protein or peptide, but which maintains the basic protein and side chain structure of the naturally occurring form, and/or which maintains a basic three-dimensional structure of at least a biologically active portion (e.g., the thioredoxin active site) of the native protein. Such changes include, but are not limited to: changes in one or a few amino acid side chains; changes one or a few amino acids, including deletions (e.g., a truncated version of the protein or peptide (fragment)), insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. According to the present invention, any protein or peptide useful in the present invention, including homologues of natural thioredoxin proteins, have a thioredoxin active-site such that, in reduced state, the protein or peptide is capable of participating in redox reactions through the reversible oxidation of its active-site dithiol to a disulfide, of catalyzing dithiol-disulfide exchange reactions, and/or of decreasing the viscosity or cohesivity of mucus or sputum or increasing the liquefaction of mucus or sputum. As used herein, a protein or peptide containing a thioredoxin active-site can have characteristics similar to thioredoxin, and preferably, is thioredoxin selected from the group of prokaryotic thioredoxin, yeast thioredoxin, plant thioredoxin, or mammalian thioredoxin. In a particularly preferred embodiment, the protein is human thioredoxin.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in homologues, as compared to the wild-type protein, either agonize, antagonize, or do not substantially change, the basic biological activity of the homologue as compared to the naturally occurring protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

In one embodiment, homologues of a thioredoxin protein, including peptide and non-peptide homologues of thioredoxin, can be products of drug design or selection and can be produced using various methods known in the art. Such homologues can be referred to as mimetics. A mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In one embodiment of the present invention, a protein suitable for use in the present invention has an amino acid sequence that comprises, consists essentially of, or consists of a full length sequence of a thioredoxin protein or any fragment thereof that has a thioredoxin active site as described herein. For example, any one of SEQ ID NOs:4-12 or a fragment or other homologue thereof that contains a thioredoxin active site as described herein is encompassed by the invention. Such homologues can include proteins having an amino acid sequence that is at least about 10% identical to the amino acid sequence of a full-length thioredoxin protein, or at least 20% identical, or at least 30% identical, or at least 40% identical, or at least 50% identical, or at least 60% identical, or at least 70% identical, or at least 80% identical, or at least 90% identical, or greater than 95% identical to the amino acid sequence of a full-length thioredoxin protein, including any percentage between 10% and 100%, in whole integers (10%, 11%, 12%, . . . 98%, 99%, 100%).

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
  Reward for match=1
  Penalty for mismatch=−2
  Open gap (5) and extension gap (2) penalties
  gap x_dropoff (50) expect (10) word size (11) filter (on)
For blastp, using 0 BLOSUM62 matrix:
  Open gap (11) and extension gap (1) penalties
  gap x_dropoff (50) expect (10) word size (3) filter (on).

A protein useful in the present invention can also include proteins having an amino acid sequence comprising at least 10 contiguous amino acid residues of any full-length thioredoxin protein (e.g., SEQ ID NOs:4-12) (i.e., 10 contiguous amino acid residues having 100% identity with 10 contiguous amino acids of a reference sequence). In other embodiments, a homologue of a thioredoxin protein includes amino acid sequences comprising at least 15, or at least 20, or at least 25, or at least 30, or at least 35, or at least 40, or at least 45, or at least 50, or at least 55, or at least 60, or at least 65, or at least 70, or at least 75, or at least 80 contiguous amino acid residues of the amino acid sequence of a naturally occurring thioredoxin protein, and so on, up to the full-length of the protein, including any intervening length in whole integers (10, 11, 12, . . . ).

According to the present invention, the term "contiguous" or "consecutive", with regard to sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a protein useful in the present invention includes a protein having an amino acid sequence that is sufficiently similar to a natural thioredoxin amino acid sequence that a nucleic acid sequence encoding the homologue is capable of hybridizing under moderate, high or very high stringency conditions (described below) to (i.e., with) a nucleic acid molecule encoding the natural thioredoxin protein (i.e., to the complement of the nucleic acid strand encoding the natural thioredoxin amino acid sequence). Such hybridization conditions are described in detail below.

A nucleic acid sequence complement of nucleic acid sequence encoding a thioredoxin protein of the present invention refers to the nucleic acid sequence of the nucleic acid strand that is complementary to the strand which encodes thioredoxin. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes an amino acid sequence of a thioredoxin protein, and/or with the complement of the nucleic acid sequence that encodes such amino acid sequence. Methods to deduce a complementary sequence are known to those skilled in the art.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

A protein of the present invention can also be a fusion protein that includes a segment containing a thioredoxin active-site and a fusion segment that can have a variety of functions. For example, such a fusion segment can function as a tool to simplify purification of a protein of the present invention, such as to enable purification of the resultant fusion protein using affinity chromatography. A suitable fusion segment can be a domain of any size that has the desired function (e.g., imparts increased stability to a protein, imparts increased immunogenicity to a protein, and/or simplifies purification of a protein). It is within the scope of the present invention to use one or more fusion segments. Fusion segments can be joined to amino and/or carboxyl termini of the segment containing a thioredoxin active-site. Linkages between fusion segments and thioredoxin active-site-containing domains of fusion proteins can be susceptible to cleavage in order to enable straight-forward recovery of the thioredoxin active-site-containing domains of such proteins. Fusion proteins are preferably produced by culturing a recombinant cell transformed with a fusion nucleic acid molecule that encodes a protein including the fusion segment attached to either the carboxyl and/or amino terminal end of an thioredoxin active-site-containing domain.

In one embodiment, a protein or peptide containing a thioredoxin active-site suitable for use with the method of the present invention comprises a protein or peptide containing a thioredoxin active-site derived from a substantially similar species of animal as that to which the protein is to be administered. In another embodiment, any protein or peptide containing a thioredoxin active-site, including from diverse sources such as microbial and plant, can be used in a given patient.

In one embodiment of the present invention, any of the amino acid sequences described herein, such as the amino acid sequence of a naturally occurring thioredoxin protein, can be produced with from at least one, and up to about 20, additional heterologous amino acids flanking each of the C- and/or N-terminal ends of the specified amino acid sequence.

The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

In another embodiment, a protein or peptide containing a thioredoxin active-site suitable for use with the method of the present invention comprises an isolated, or biologically pure, protein which has been removed from its natural milieu. As such, "isolated" and "biologically pure" do not necessarily reflect the extent to which the protein has been purified. An isolated protein of the present invention can, for example, be obtained from its natural source, be produced using recombinant DNA technology (e.g., polymerase chain reaction (PCR) amplification, cloning), or be synthesized chemically.

Preferably, the protein containing a thioredoxin active site to be used in methods of the invention have a half-life in vivo that is sufficient to cause a measurable or detectable increase in liquefaction (or decrease in the viscosity or cohesivity) of mucus or sputum in a patient, and or to cause a measurable, detectable or perceived therapeutic benefit to the patient that is associated with the mucus and sputum in the patient. Such half-life can be effected by the method of delivery of such a protein. A protein of the present invention preferably has a half-life of greater than about 5 minutes in an animal, and more preferably greater than about 4 hours in an animal, and even more preferably greater than about 16 hours in an animal. In a preferred embodiment, a protein of the present invention has a half-life of between about 5 minutes and about 24 hours in an animal, and preferably between about 2 hours and about 16 hours in an animal, and more preferably between about 4 hours and about 12 hours in an animal.

Further embodiments of the present invention include nucleic acid molecules that encode a protein or peptide containing a thioredoxin active site. Such nucleic acid molecules can be used to produce a protein that is useful in the method of the present invention in vitro or in vivo. A nucleic acid molecule of the present invention includes a nucleic acid molecule comprising, consisting essentially of, or consisting of, a nucleic acid sequence encoding any of the proteins described previously herein. In accordance with the present invention, an isolated nucleic acid molecule is a nucleic acid molecule (polynucleotide) that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. An isolated nucleic acid molecule of the present invention can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode the desired protein of the present invention or to form stable hybrids under stringent conditions with natural gene isolates. An isolated nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a given protein useful in the present invention can vary due to degeneracies.

According to the present invention, reference to a gene includes all nucleic acid sequences related to a natural (i.e. wild-type) gene, such as regulatory regions that control production of the protein encoded by that gene (such as, but not limited to, transcription, translation or post-translation control regions) as well as the coding region itself. In another embodiment, a gene can be a naturally occurring allelic variant that includes a similar but not identical sequence to the nucleic acid sequence encoding a given protein. Allelic variants have been previously described above. The phrases "nucleic acid molecule" and "gene" can be used interchangeably when the nucleic acid molecule comprises a gene as described above.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on protein biological activity. Allelic variants and protein homologues (e.g., proteins encoded by nucleic acid homologues) have been discussed in detail above.

A nucleic acid molecule homologue can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Another method for modifying a recombinant nucleic acid molecule encoding a given protein is gene shuffling (i.e., molecular breeding) (See, for example, U.S. Pat. No. 5,605,793 to Stemmer; Minshull and Stemmer; 1999, Curr. Opin. Chem. Biol. 3:284-290; Stemmer, 1994, P.N.A.S. USA 91:10747-10751, all of which are incorporated herein by reference in their entirety). This technique can be used to efficiently introduce multiple simultaneous changes in the protein. Nucleic acid molecule homologues can be selected by hybridization with an given gene or by screening the function of a protein encoded by a nucleic acid molecule (i.e., biological activity).

One embodiment of the present invention relates to a recombinant nucleic acid molecule which comprises the isolated nucleic acid molecule described above which is operatively linked to at least one transcription control sequence. More particularly, according to the present invention, a recombinant nucleic acid molecule typically comprises a recombinant vector and the isolated nucleic acid molecule as described herein. According to the present invention, a recombinant vector is an engineered (i.e., artificially produced) nucleic acid molecule that is used as a tool for manipulating a nucleic acid sequence of choice and/or for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is, nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid sequences of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell, although it is preferred if the vector remain separate from the genome for most applications of the invention. The entire vector can remain in place within a host cell, or under certain conditions, the plasmid DNA can be deleted, leaving behind the nucleic acid molecule of the present invention. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., the protein containing a thioredoxin active site) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

In another embodiment of the invention, the recombinant nucleic acid molecule comprises a viral vector. A viral vector includes an isolated nucleic acid molecule of the present invention integrated into a viral genome or portion thereof, in which the nucleic acid molecule is packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

Typically, a recombinant nucleic acid molecule includes at least one nucleic acid molecule of the present invention operatively linked to one or more expression control sequences. As used herein, the phrase "recombinant molecule" or "recombinant nucleic acid molecule" primarily refers to a nucleic acid molecule or nucleic acid sequence operatively linked to an expression control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence in a manner such that the molecule is able to be expressed when transfected (i.e., transformed, transduced, transfected, conjugated or conduced) into a host cell. Transcription control sequences are expression control sequences that control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced. Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells or plants. In microbial systems, the term "transformation" is used to describe an inherited change due to the acquisition of exogenous nucleic acids by the microorganism and is essentially synonymous with the term "transfection." However, in animal cells, transformation has acquired a second meaning which can refer to changes in the growth properties of cells in culture (described above) after they become cancerous, for example. Therefore, to avoid confusion, the term "transfection" is preferably used with regard to the introduction of exogenous nucleic acids into animal cells, and is used herein to generally encompass transfection of animal cells and transformation of plant cells and microbial cells, to the extent that the terms pertain to the introduction of exogenous nucleic acids into a cell. Therefore, transfection techniques include, but are not limited to, transformation, particle bombardment, electroporation, microinjection, lipofection, adsorption, infection and protoplast fusion.

One or more recombinant molecules of the present invention can be used to produce an encoded product (e.g., a protein containing a thioredoxin active site) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell.

In a preferred embodiment, a protein or peptide containing a thioredoxin active site in reduced state is contacted with the mucus or sputum to be treated in a composition. The composition comprises the protein containing a thioredoxin active site, and may include one or more additional compounds, such as other compounds that can be used to reduce excessively viscous or cohesive mucus or sputum or increase the liquefaction of such mucus or sputum. In one embodiment, a composition can be used to delivery a nucleic acid molecule encoding a protein or peptide containing a thioredoxin active site to a cell in the patient to be treated (e.g., an epithelial cell in the lung or airways), such that the cell can become transfected with and express the protein, and so that the protein can contact mucus or sputum in the microenvironment of the cell.

A composition can also include, for example, a pharmaceutically acceptable carrier, which includes pharmaceutically acceptable excipients and/or delivery vehicles, for delivering a protein or nucleic acid molecule or other regulatory compound to a patient. As used herein, a pharmaceutically acceptable carrier refers to any substance suitable for delivering a therapeutic protein, nucleic acid or other compound useful in the method of the present invention to a suitable in vivo or ex vivo site. Preferred pharmaceutically acceptable carriers are capable of maintaining a protein, nucleic acid molecule or compound in a form that, upon arrival of the protein, nucleic acid molecule or compound at the desired site (e.g., the site where the mucus or sputum to be treated is secreted or drains), is capable of contacting the mucus or sputum (in the case of a protein or compound) or of entering the cell and being expressed by the cell (in the case of a nucleic acid molecule) so that the expressed protein can contact the mucus or sputum. Suitable excipients of the present invention include excipients or formularies that transport or help transport, but do not specifically target a therapeutic agent (protein, nucleic acid or compound) to a cell, tissue or fluid (mucus or sputum) (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into a patient. As used herein, a controlled release formulation comprises one or more therapeutic agents of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Suitable delivery vehicles for nucleic acids include, but are not limited to liposomes, viral vectors or other delivery vehicles, including ribozymes.

A liposome delivery vehicle comprises a lipid composition that is capable of delivering a protein, compound or nucleic acid molecule to a suitable cell and/or tissue in a patient. A liposome delivery vehicle can comprise a lipid composition that is capable of fusing with the plasma membrane of a cell to deliver the composition into a cell. A liposome delivery vehicle is preferably capable of remaining stable in a patient for a sufficient amount of time to deliver a composition to a preferred site in the patient. Suitable liposomes for use with the present invention include any liposome.

A suitable, or effective, amount of a protein or peptide containing a thioredoxin active-site to administer to a patient is an amount that is capable of: participating in redox reactions through the reversible oxidation of its active-site dithiol to a disulfide, catalyzing dithiol-disulfide exchange reactions, and particularly, decreasing the viscosity or cohesivity of mucus or sputum and/or increasing the liquefaction of mucus or sputum in a patient, and more particularly, increasing the liquefaction of mucus or sputum in a patient sufficient to provide a therapeutic benefit to the patient. Decreases in the viscosity or cohesivity or increases in the liquefaction of mucus or sputum can be measured, detected or determined as described previously herein or by any suitable method known to those of skill in the art.

In one embodiment, a preferred amount of a protein or peptide containing a thioredoxin active-site to be administered to a patient comprises between about 0.1 micromoles×kilogram$^{-1}$ and about 150 micromoles×kilogram$^{-1}$ body weight of a patient. In another embodiment, a preferred amount of a protein or peptide containing a thioredoxin active-site to be administered to a patient comprises between about 1.5 micromoles×kilogram$^{-1}$ and about 150 micromoles×kilogram$^{-1}$ body weight of a patient. A more preferred amount of a protein or peptide containing a thioredoxin active-site to be administered to a patient comprises between about 2 micromoles×kilogram$^{-1}$ and about 25 micromoles×kilogram$^{-1}$ body weight of a patient. An even more preferred amount of a protein or peptide containing a thioredoxin active-site to be administered to a patient comprises between about 3 micromoles×kilogram$^{-1}$ and about 10 micromoles×kilogram$^{-1}$ body weight of a patient.

In another embodiment, if the route of delivery is aerosol or a similar route, an amount of a protein or peptide containing a thioredoxin active-site to be administered to a patient comprises at least about 0.25 mg per dosing unit (e.g., a dosing unit for a human is typically about 2-3 ml) and about 25 mg per dosing unit. Preferably, an amount of a protein or peptide containing a thioredoxin active-site to be administered to a patient comprises at least about 0.25 mg per dosing unit, and more preferably at least about 0.3 mg per dosing unit, and more preferably at least about 0.35 mg per dosing unit, and so on, in increments of 0.05 mg, up to greater than 25 mg per dosing unit. For aerosol delivery, typically, only about 10% of the volume in the aerosol is actually delivered to the airway. Therefore, for other routes of administration when the volume of the composition that will be delivered to the site is greater, it will readily be seen that lower doses of the protein or peptide comprising a thioredoxin active site may be used.

The optimum amount of a protein of the present invention to be administered to an animal will vary depending on the route of administration. For instance, if the protein is administered by an inhaled (aerosol) route, the optimum amount to be administered may be different than the optimum amount to be administered by intratracheal injection. It is within the ability of one skilled in the art to vary the amount depending on such route of administration. It is important to note that a suitable amount of a protein of the present invention is an amount that has the desired function without being toxic to an animal.

In a preferred embodiment of the present invention, a composition of the present invention that contains a protein comprising a thioredoxin reactive site is further formulated with one or more agents comprising a reducing system that maintains or reduces the thioredoxin active site in the protein to the reduced state. Preferably, such an agent includes nicotinamide-adenine dinucleotide phosphate (reduced form) (NADPH) and/or thioredoxin reductase, with formulation with NADPH being particularly preferred. The present inventor has found that the presence of a reducing system with a protein or peptide containing a thioredoxin active site significantly increases the ability of the protein containing a thioredoxin active site to function in the method of the invention (e.g. to increase the liquefaction of mucus or sputum). In addition, the present inventor has found that it is sufficient to include NADPH as the reducing system, and therefore, thioredoxin reductase is not a necessary component of the reducing system, but can be included, if desired. Other reducing systems can be used in the present invention and include, but are not limited to, NADH-dependent thioredoxin reductase, lipoic acid, and other biological reductants. In general, the present inventor contemplates that an original source of reducing equivalents, most likely NADPH or NADH, will be an important component of a composition of the present invention for optimal therapeutic benefit. However, additional component(s) which serve an intermediary function of transferring the reducing equivalents (H$^+$, from NADPH or NADH) to the thioredoxin or thioredoxin active site-containing molecule, also can be used.

When NADPH is included in a composition of the present invention, the composition is preferably formulated with between about 0.5 µM and about 20 mM achieved surface concentration of NADPH, and more preferably, between about 5 µM and about 2 mM achieved surface concentration of NADPH, and even more preferably, between about 50 µM and about 200 µM achieved surface concentration of NADPH. In another embodiment, the composition can be formulated with any suitable amount of NADPH, preferably between about 0.5 µM and about 20 mM achieved surface concentration of NADPH in increments of 0.1 µM (i.e., 0.5 µM, 0.6 µM, . . . 19.9 µM, 20 µM). An "achieved surface concentration" is the concentration of a particular chemical, such as NADPH, that is achieved, or present, at the surface of a cell or tissue, for example, at the surface of lung epithelial lining. Therefore, it may be necessary to actually administer a larger concentration of a particular chemical in order to achieve a certain surface concentration. It is well within the ability of one skilled in the art to determine such concentrations. When thioredoxin reductase in included in a composition of the present invention, it is preferably formulated with between about 0.001 µM and about 1 µM achieved surface concentration of thioredoxin reductase, and more preferably, between about 0.001 µM and about 0.1 µM achieved surface concentration of thioredoxin reductase, including any amount between about 0.0001 µM and 1 µM, in increments of 0.001 µM. In one embodiment, it is not necessary to include any thioredoxin reductase in a composition of the invention. It is within the scope of the present invention that such amounts of thioredoxin reductase and/or NADPH can be modified by one skilled in the art in order to maintain or enhance the reduced state of a thioredoxin active-site, as the amount of a protein or peptide containing such active-site or the mode of delivery indicates.

As discussed above, a composition of the invention can include one or more additional compounds, such as other compounds that can be used to reduce excessively viscous or cohesive mucus or sputum or increase the liquefaction of such mucus or sputum. Examples of such compounds are known in the art and include, but are not limited to, purified rhDNase, N-acetylcysteine, nacystelyn (an N-acetyl-L-cysteine derivative), and gelsolin.

As discussed above, a composition of the present invention is administered to a patient in a manner effective to deliver the composition, and particularly the protein comprising a thioredoxin active site, a recombinant nucleic acid molecule comprising a nucleic acid sequence encoding a protein or peptide containing a thioredoxin active site, and/or any other compounds in the composition, to a target site (e.g., mucus or sputum to be treated for proteins and compounds, a target host cell that will be or is in the environment of the mucus or sputum to be treated for recombinant nucleic acid molecules). Suitable administration protocols include any in vivo or ex vivo administration protocol.

According to the present invention, an effective administration protocol (i.e., administering a composition of the present invention in an effective manner) comprises suitable dose parameters and modes of administration that result in contact of the protein containing a thioredoxin active site and/or other compound in the composition with the mucus or sputum to be treated, or in the transfection and expression of a recombinant nucleic acid molecule encoding a protein comprising a thioredoxin active site in a desired host cell of a patient, preferably so that the patient obtains some measurable, observable or perceived benefit from such administration. In some situations, by sampling the mucus or sputum from the patient, effective dose parameters can be determined using methods as described herein for assessment of mucus or sputum viscosity or liquefaction. Alternatively, effective dose parameters can be determined by experimentation using in vitro samples, in vivo animal models, and eventually, clinical trials if the patient is human. Effective dose parameters can be determined using methods standard in the art for a particular disease or condition. Such methods include, for example, determination of survival rates, side effects (i.e., toxicity) and progression or regression of disease.

According to the present invention, suitable methods of administering a composition of the present invention to a patient include any route of in vivo administration that is suitable for delivering the composition to the desired site into a patient. The preferred routes of administration will be apparent to those of skill in the art, depending on whether the compound is a protein, nucleic acid, or other compound (e.g., a drug), to what part of the body the composition is to be administered, and the disease or condition experienced by the patient. In general, methods of in vivo administration include, but are not limited to, intravenous administration, intraperitoneal administration, intramuscular administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracerebral, nasal, oral, pulmonary administration, impregnation of a catheter, and direct injection into a tissue. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992, which is incorporated herein by reference in its entirety). Oral delivery can include solids and liquids that can be taken through the mouth, for example, as tablets or capsules, as well as being formulated into food and beverage products. Other routes of administration that are useful for mucosal tissues include bronchial, intradermal, intramuscular, intranasal, other inhalatory, rectal, subcutaneous, topical, transdermal, vaginal, transcervical, pericervical and urethral routes. In addition, administration protocols can include pretreatment devices, such as application of the protein, peptide or composition in a diaphragm (e.g., to the cervix) for use in applications such as infertility. In a preferred embodiment of the present invention, when the protein or composition of the invention is administered to treat excessively or abnormally viscous or cohesive sputum or mucus in the respiratory tract (airways), a protein or peptide (or composition) containing a thioredoxin active-site or other compound is administered by a route including, but not limited to, inhalation (i.e. by inhaling an aerosol, e.g., in or with surfactants); direct installation into the lung via a bronchoscope, endotracheal tube and/or via any artificial ventilation device; nasal administration (intranasal or transnasal), bronchial, or intratracheally (i.e. by injection directly into the trachea or tracheostomy), either directly or via lipid-encapsulation or surfactant. Any conceivable method of introducing the composition or protein into the airways so that it can contact the mucus or sputum therein is encompassed by the invention.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention.

For example, using liposome delivery, U.S. Pat. No. 5,705,151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. In addition, Liu et al., *Nature Biotechnology* 15:167, 1997, demonstrated that intravenous delivery of cholesterol-containing cationic liposomes containing genes preferentially targets pulmonary tissues and effectively mediates transfer and expression of the genes in vivo. Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949-959; Kaneda et al., 1997, *Ann N.Y. Acad. Sci.* 811: 299-308; and von der Leyen et al., 1995, *Proc Natl Acad Sci USA* 92:1137-1141).

Delivery of numerous nucleic acid sequences has been accomplished by administration of viral vectors encoding the nucleic acid sequences. Using such vectors, successful delivery and expression has been achieved using ex vivo delivery (See, of many examples, retroviral vector; Blaese et al., 1995, *Science* 270:475-480; Bordignon et al., 1995, *Science* 270:470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426-1431). A publication by Maurice et al. (1999, *J. Clin. Invest.* 104:21-29) demonstrated that an adenoviral vector encoding a β2-adrenergic receptor, administered by intracoronary delivery, resulted in diffuse multichamber myocardial expression of the gene in vivo, and subsequent significant increases in hemodynamic function and other improved physiological parameters. Levine et al. describe in vitro, ex vivo and in vivo delivery and expression of a gene to human adipocytes and rabbit adipocytes using an adenoviral vector and direct injection of the constructs into adipose tissue (Levine et al., 1998, *J. Nutr. Sci. Vitaminol.* 44:569-572).

In the area of neuronal gene delivery, multiple successful in vivo gene transfers have been reported. Millecamps et al. reported the targeting of adenoviral vectors to neurons using neuron restrictive enhancer elements placed upstream of the promoter for the transgene (phosphoglycerate promoter). Such vectors were administered to mice and rats intramuscularly and intracerebrally, respectively, resulting in successful neuronal-specific transfection and expression of the transgene in vivo (Millecamps et al., 1999, *Nat. Biotechnol.* 17:865-869). As discussed above, Bennett et al. reported the use of adeno-associated viral vector to deliver and express a gene by subretinal injection in the neural retina in vivo for greater than 1 year (Bennett, 1999, ibid.).

Gene delivery to synovial lining cells and articular joints has had similar successes. Oligino and colleagues report the use of a herpes simplex viral vector which is deficient for the immediate early genes, ICP4, 22 and 27, to deliver and express two different receptors in synovial lining cells in vivo (Oligino et al., 1999, *Gene Ther.* 6:1713-1720). The herpes vectors were administered by intraarticular injection. Kuboki et al. used adenoviral vector-mediated gene transfer and intraarticular injection to successfully and specifically express a gene in the temporomandibular joints of guinea pigs in vivo (Kuboki et al., 1999, *Arch. Oral. Biol.* 44:701-709). Apparailly and colleagues systemically administered adenoviral vectors encoding IL-10 to mice and demonstrated successful expression of the gene product and profound therapeutic effects in the treatment of experimentally induced arthritis (Apparailly et al., 1998, *J. Immunol.* 160:5213-5220). In another study, murine leukemia virus-based retroviral vector was used to deliver (by intraarticular injection) and express a human growth hormone gene both ex vivo and in vivo (Ghivizzani et al., 1997, *Gene Ther.* 4:977-982). This study showed that expression by in vivo gene transfer was at least equivalent to that of the ex vivo gene transfer. As discussed above, Sawchuk et al. has reported successful in vivo adenoviral vector delivery of a gene by intraarticular injection, and prolonged expression of the gene in the synovium by pretreatment of the joint with anti-T cell receptor monoclonal antibody (Sawchuk et al., 1996, ibid. Finally, it is noted that ex vivo gene transfer of human interleukin-1 receptor antagonist using a retrovirus has produced high level intraarticular expression and therapeutic efficacy in treatment of arthritis, and is now entering FDA approved human gene therapy trials (Evans and Robbins, 1996, *Curr. Opin. Rheumatol.* 8:230-234). Therefore, the state of the art in gene therapy has led the FDA to consider human gene therapy an appropriate strategy for the treatment of at least arthritis. Taken together, all of the above studies in gene therapy indicate that delivery and expression of a recombinant nucleic acid molecule according to the present invention is feasible.

Another method of delivery of recombinant molecules is in a non-targeting carrier (e.g., as "naked" DNA molecules, such as is taught, for example in Wolff et al., 1990, *Science* 247, 1465-1468). Such recombinant nucleic acid molecules are typically injected by direct or intramuscular administration. Recombinant nucleic acid molecules to be administered by naked DNA administration include an isolated nucleic acid molecule of the present invention, and preferably includes a recombinant molecule of the present invention that preferably is replication, or otherwise amplification, competent. A naked nucleic acid reagent of the present invention can comprise one or more nucleic acid molecules of the present invention including a dicistronic recombinant molecule. Naked nucleic acid delivery can include intramuscular, subcutaneous, intradermal, transdermal, intranasal and oral routes of administration, with direct injection into the target tissue being most preferred. A preferred single dose of a naked nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 μm in diameter) and are propelled into skin cells or muscle with a "gene gun."

In the method of the present invention, therapeutic compositions can be administered to any member of the Vertebrate class, Mammalia, including, without limitation, primates, rodents, livestock and domestic pets. Preferred patients to protect are humans.

The following examples are provided for the purpose of illustration and are not intended to limit the scope of the present invention.

EXAMPLES

The following Materials and Methods were used in Examples 1-6 below.

Reagents and Materials.

Lyophilized recombinant *E. coli* Trx was obtained from Promega (Madison, Wis.). *E. coli* TR was from American Diagnostica, (Greenwich, Conn.). β-Nicotinamide adenine dinucleotide phosphate, reduced form (NADPH), reduced GSH, glutathione reductase, dithiothreitol, disopropylfluorophosphate, aprotinin, N-ethyl maleimide, schiff reagent, salmon testes DNA, and Hoechst dye were all obtained from Sigma Chemical (St. Louis, Mo.). N-acetylcysteine was from Fisher Scientific (Pittsburgh, Pa.). All other chemicals were of the highest possible grade.

Sputum Collection.

Sputum was obtained from adult and pediatric patients with CF at National Jewish Medical and Research Center (Denver, Colo.) and the Children's Hospital (Denver, Colo.). Patients were diagnosed with CF if they had sweat chloride values in excess of 60 mM in two separate pilocarpine iontophoresis sweat tests, and exhibited two allelic CF-producing mutations in subsequent genetic analysis. All samples were donated by either spontaneous expectoration or hypertonic saline induction. Sputum samples containing visibly detectable saliva were discarded. After expectoration, samples were stored at −80° C. until their time of use. Sputum collection protocol, data collection, and consent/assent forms were approved by the Institutional Review Board of the University of Colorado Health Science Center (COMIRB) and affiliated hospitals.

Compaction Assay.

CF sputum stored at −80° C. was thawed at room temperature and aliquoted into 1.5 ml Eppendorf centrifuge tubes at volumes of 275 µl using a positive displacement pipette (Rainin, Emeryville, Calif.). Sputum samples were subjected to either diluent ($H_2O$), Trx+TR+NADPH, GSH+glutathione reductase+NADPH, dithiothreitol (DTT) or N-acetylcysteine treatment by the addition of 25 µl of $H_2O$ containing the appropriate molar concentration of each agent. After brief vortexing (~1 second), sample tubes were loaded onto a microtube rotisserie (Barnstead, Dubuque, Iowa) and incubated at 37° C. for 20 minutes. Samples were then processed for compaction assay according to methodology originated by Daugherty et al. (Daugherty et al., *Biomaterials* 16:553-558, 1995). To perform the assay, the contents of each sample were loaded into 100 µl glass micro-capillary tubes (Fisher Scientific) that had been previously welded to 200 µl pipette tips in order to achieve a tight fit. Three modified capillary tubes were used to draw up >90% of each sputum sample. Capillary tubes were then removed from their pipette tip, sealed with clay, and centrifuged for 10 minutes in a hematocrit centrifuge (IEC, Needham Heights, Mass.), followed by measurement of the length in millimeters of the gel (solid) and aqueous (liquid) phases in each tube. The percent liquid fraction of each capillary tube was calculated by dividing aqueous phase length by total length (gel+aqueous)×100. The three measurements of the liquid fraction (%) derived from each sample were then averaged to generate a single value for each treatment condition.

Magnetic Microrheometry.

Viscoelastic change in response to treatment was measured by means of a magnetic microrheometer as developed by King (King M., Magnetic microrheometer. In: *Methods in Bronchial Mucology*, edited by Braga P C, and Allegra L. New York: Raven Press, 1988, p. 73-83). An 80-120 µm steel sphere was placed in a 10 mg sputum sample. An electromagnet was used to oscillate this sphere, whose image was projected onto a pair of photocells via a microscope. The mucus retarded the motion of the sphere and this effect was revealed by plotting the motion of the sphere against the driving force of the magnet on an oscilloscope, from which G* was measured. G* was the mechanical impedance or vector sum of viscosity and elasticity. For Trx and NADPH dose response experiments, log G* at 10 rad/s was measured before any treatment (baseline), and then after 20 minute incubation with no treatment, diluent ($H_2O$), or Trx with reducing system. All treatments were administered to the sample in a volume of $H_2O$ equal to 10% of total sample volume. One measurement was performed per aliquot of sample.

Glycoprotein Extraction from Sputum.

Extraction of soluble glycoproteins from sputum was performed according to methodology outlined by Davies et al. (Davies and Carlstedt, *Methods Mol Biol* 125:3-13, 2000). 275 µl of CF sputum was treated for 20 minutes at 37° C. with 25 µl of $H_2O$ alone or $H_2O$ containing Trx (10 or 30 µM)+ NADPH (2 mM) and TR (0.1 µM). After treatment, 100 µl of $H_2O$ containing 1 mM disopropylfluorophosphate and 10 µg ml aprotinin, was added to each sample, followed by 15 minute centrifugation at 22,000 g at 4° C. The resulting supernatant (aqueous phase) of each sample was transferred to a new microcentrifuge tube and stored at −20° C. The remaining solid gel portion of each sample was carefully unseated from the tube bottom in the presence of 250 µl of guanidinium extraction buffer (6 M guanidinium chloride; 5 mM EDTA; 10 mM sodium phosphate buffer, pH 6.5; 1 mM N-ethyl maleimide; 100 µM disopropylfluorophosphate; and 1 µg/ml aprotinin) using a pipette tip and rotated for 14 hours at 4° C. After centrifugation, the resulting supernatant from this gel phase extraction was then transferred to a clean tube and frozen at −20° C. until time of electrophoresis.

Analysis of Glycoprotein Content.

The glycoprotein content of aqueous and gel phase samples were evaluated by staining with periodic acid Schiff reagent (PAS) according to methodology outlined by Thornton et al. (Thornton et al., *Methods Mol Biol* 125:77-85, 2000). Aqueous and gel samples were thawed and 80 µl aliquots of each were loaded onto a 1.0% agarose gel (150 mm×125 mm) housed within a Biomax horizontal electrophoresis apparatus (Kodak, Rochester, N.Y.). Electrophoresis reagents were as follows: electrophoresis buffer: 40 mM Tris-acetate, 1 mM EDTA, pH 8.0, 0.1% SDS; sample loading buffer: 60% electrophoresis buffer, 40% glycerol (v/v) and 0.005% (w/v) bromophenol blue. Gel contents were transferred to polyvinylidene (PVDF) membrane by vacuum blotter (Boeckel Scientific, Feasterville, Pa.) using 0.6 M NaCl, 60 mM sodium citrate as a transfer solution. After transfer, membranes were washed in three changes of water and transferred to 200 ml of a 1% periodic acid (v/v) 3% acetic acid (v/v) solution for 30 minutes at room temperature. The membrane was then rinsed twice with 0.1% sodium metabsulfite in 1 mM HCl and placed in Schiff reagent for 6 minutes.

Measurement of Total DNA Content.

275 µl of CF sputum was incubated with no treatment, 25 µl of $H_2O$, or 25 µl of $H_2O$ containing Trx (30 µM)+TR (0.1 µM) and NADPH (2 mM). After 20 minute incubation at 37° C., 100 µl of $H_2O$ was added to each sample, followed by centrifugation (22,000×g) for 10 minutes. Resulting gel and liquid phases were separated and incubated with an equal volume of digestion solution consisting of 100 mM Tris Cl, 5 mM EDTA, 200 mM NaCl, 0.5% Tween 20, and 1 mg/ml proteinase K for 4 hours at 50° C. DNA was purified from liquid and gel phases by phenol/chloroform extraction and resuspended in 100 µl of TE buffer, pH 8.0. DNA concentrations were determined by Hoechst assay (Labarca and Paigen, *Anal Biochem* 102:344-352, 1980) using an F-2000 fluorometer (Hitachi, Schaumburg, Ill.) with an excitation wavelength of 575 nM and an emission wavelength of 555 nm. Salmon testis DNA, dissolved in TE buffer, was used to establish the standard curve.

Statistics. Data in the figures are presented as mean±standard deviations, except FIGS. 4A and 4B which displays standard error. A linear mixed-effects modeling approach was used to analyze the effect of treatments on the liquefaction, viscoelasticity, and DNA solubility of sputum samples. Dunnet's correction was applied when comparing several treatments against a single control. Reproducibility of the compaction assay was assessed via intraclass correlation coefficients calculated in the linear model. All analyses were performed using SAS version 8.2 (SAS Institute Inc, Cary, N.C.). Significance was defined as $p<0.05$.

Example 1

The following example describes the effect of the Trx reducing system on release of liquid from CF sputum.

Due to abnormal ion transport caused by defects in the CFTR gene, airway secretions in CF patients are often desiccated. As a consequence, purulent CF sputum is comprised largely of a rigid and nonflowing biopolymer matrix, often referred to as gel phase, and lesser amounts of soluble, liquid phase. To assess the effect of Trx on the ratios of these two phases in sputum, compaction assay measurements were performed. In a first experiment, equal volumes of sputum samples were treated with 25 μl H$_2$O containing 0, 1, 10, or 30 μM Trx; 0.1 μM TR; and 2 mM NADPH (final concentration). After 20 minute incubation, the liquid fraction of each sample was determined by compaction assay.

The mean (±SD) percentage of CF sputum present in the liquid phase was 3.5±2.9% prior to Trx exposure (FIG. 1A; values are the mean from 5 independent experiments. *P<0.05 versus H$_2$O exposed samples). Aliquots treated with diluent (H$_2$O) equal to 10% of the sputum demonstrated a small, nonsignificant increase (6.2±6.6%) in the proportion of sputum present in the liquid phase. In contrast, the liquid phase of CF sputum was significantly increased after treatment with the Trx reducing system (Trx+0.1 μM TR, and 2 mM NADPH). Treatment of sputum with Trx (1 μM) increased the liquid fraction of sputum to 37.8±15.4%. Maximal increases in liquid fraction occurred in samples incubated with a higher Trx (30 μM) concentration (74.5±15.6%).

Figure 1B:
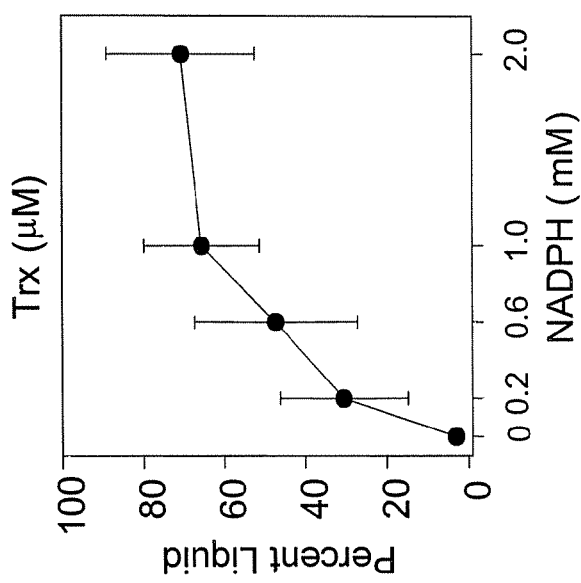
FIG. 1B is a line graph showing that liquefaction of CF sputum by Trx is dependent upon NADPH.

To examine the effect of NADPH, additional samples from different donors were treated with 30 μM Trx, 0.1 μM TR and either 0, 0.2, 0.6, 1.0 or 2 mM NADPH for 20 minutes. Samples treated with Trx and TR without NADPH had a low percentage of sputum present in the liquid phase (2.9%±1.3%). Aliquots treated with NADPH demonstrated a dose-dependent increase in the liquid fraction, with maximal increase occurring at 2 mM (70.55±18.13%) (FIG. 1B). Treatment of sputum with NADPH in the absence of Trx did not cause any increase in the proportion of sputum present in the liquid fraction (not shown).

Example 2

The following example demonstrates the reproducibility of compaction assay measurements from Example 1.

To assess the reproducibility of compaction assay measurements, sputum samples from three different CF donors were separated into aliquots and frozen. Specifically, freshly isolated CF sputum from three different donors (A, B, C) was separated into 275 μl aliquots and frozen. After thaw, aliquots were incubated without treatment, or with H$_2$O, 10 μM Trx (+0.1 μM TR and 2 mM NADPH), or dithiothreitol (DTT, 1 or 5 mM) for 20 minutes and the percent liquid measured by compaction assay. Results obtained from three independent experiments performed on each donor sample were used to evaluate assay reproducibility. On three consecutive days, aliquots were thawed, and treated with water, Trx and its reducing system, dithiothreitol (DTT), or no treatment.

As shown in FIG. 2, aliquots from donor A that had been treated with no additions or diluent (H$_2$O) had a liquid phase fraction of less than 10% of their total volume. Treatment of sputum aliquots from donor A with DTT (1 mM or 5 mM), or Trx (30 μM) with reducing system, increased the liquid fraction of these samples to greater than 90% of the total sample volume. These percent liquid fraction values of sputum samples from donor A did not fluctuate to any appreciable degree with identical treatment upon the second and third determinations in subsequent independent experiments. The extent of changes occurring in donor B and C samples in response to Trx or DTT exposure were less extensive than those occurring in sputum samples from donor A, but still differed significantly from the controls. For the sample from donor B, the 3 day range of variation in percent of sputum present in the liquid state after drug treatment was: 1 mM DTT-24-31%; 5 mM DTT-42-57%, 30 μM Trx-46-51%. For sputum from donor C, the range of percent liquid values was: 1 mM DTT-57-61%; 5 mM DTT-77-79%, 30 μM Trx-62-81%. These results show that the compaction assay has sufficient intra-sample reproducibility to validate its use as a method for measuring drug-induced liquefaction in a heterogeneous group of sputum samples.

Example 3

The following example demonstrates that Trx is a more potent sputum liquefaction agent than glutathione or N-acetylcysteine.

Figure 3A:
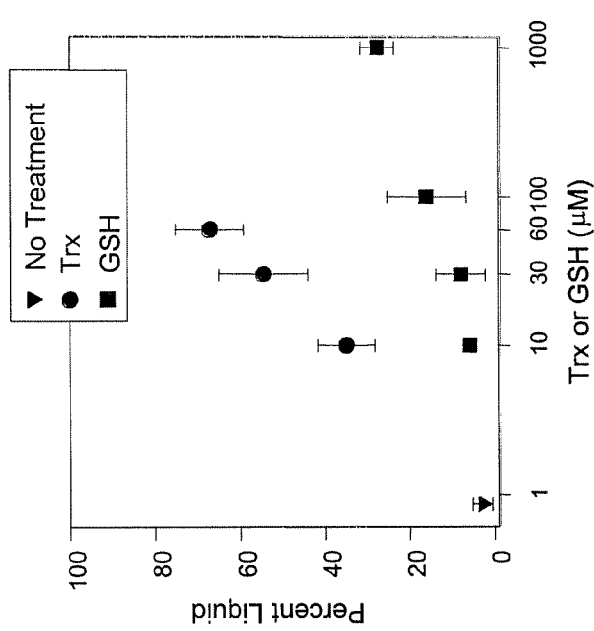
FIG. 3A is a graph showing that the Trx reducing system (Trx+0.1 µM TR+2 mM NADPH) is more potent in sputum liquefaction than a glutathione reducing system (GSH+0.1 µM Gr+2 mM NADPH).
Figure 3B:
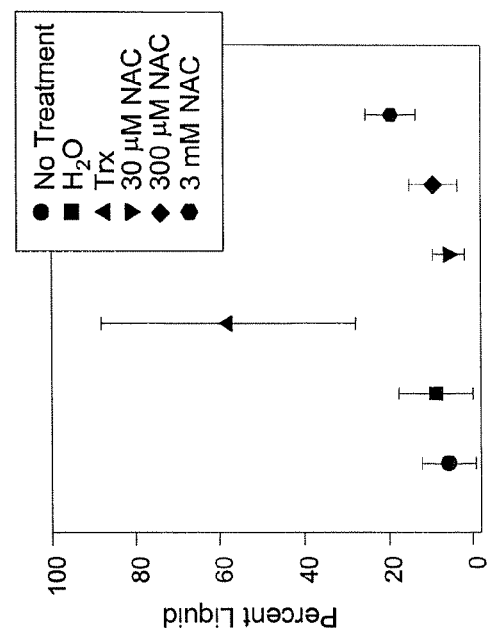
FIG. 3B is a graph showing that the Trx reducing system (Trx+0.1 µM TR+2 mM NADPH) is more potent in sputum liquefaction than N-acetylcysteine (NAC).

The effectiveness of Trx in liquefying sputum was compared with other monothiol and dithiol reducing agents. Sputum samples were aliquoted and treated with Trx or GSH for 20 minutes and percent liquid determined by compaction assay. Initial compaction assay experiments compared the potencies of the Trx and GSH reducing systems in liquefaction of sputum in the presence of equimolar concentrations of NADPH. Compared to control (no additions), a progressive and significant increase in percent liquid fraction was observed in sputum treated with 10, 30, or 60 μM Trx (FIG. 3A). In contrast, a significant increase in the liquid fraction of sputum was not observed after exposure to GSH at comparable or higher concentrations up to 1 mM. In separate studies, the use of N-acetylcysteine across a range of concentrations (FIG. 3B) also was observed to be less effective than Trx in causing liquefaction of sputum. Referring to FIGS. 3A and 3B, the actual percentages shown are as follows: No treatment=2.7±2.3%; H$_2$O=4.5±2.7%; 10 μM Trx=34.8±6.6%; 30 μM Trx=54.6±10.4%; 60 μM Trx=67.0±8.0%; 30 μM GSH=7.8±5.7%; 100 μM GSH=15.9±9.3%; 1 mM GSH=27.6±3.9%. The analysis of Trx and NAC efficacy also was determined after 20 minute incubation, but on a different set of sputum samples. Values are the mean from 5 (GSH) or 4 (NAC) experiments (*P<0.05 versus no treatment).

Example 4

The following example shows the effect of Trx reducing system on sputum viscoelasticity.

Magnetic microrheometry was performed to determine the effect of Trx and its reducing system on sputum viscosity. Measurements were performed on sputum samples before and after incubation with the Trx reducing system (Table 1) to determine the change in log G* (viscoelasticity).

TABLE 1

| Treatment | Viscoelasticity data (log G*) of untreated, H$_2$O, or thioredoxin-exposed CF sputum | | | | |
|---|---|---|---|---|---|
| | None | H$_2$O | 3 μM Trx | 10 μM Trx | 30 μM Trx |
| Before | 3.31 ± 0.05 | 3.30 ± 0.06 | 3.37 ± 0.06 | 3.33 ± 0.06 | 3.28 ± 0.04 |
| After | 3.22 ± 0.04 | 3.20 ± 0.03 | 3.11 ± 0.04 | 2.94 ± 0.05 | 2.63 ± 0.04 |

Aliquots of CF sputum were incubated, without treatment, with H$_2$O, or Trx + reducing system (0.1 μM TR and 2 μM NADPH), at 37° C. for 20 minutes.
All data are presented as log G* (mean ± standard error) for 4 samples.

In the experiment shown in FIG. 4A, sputum samples were incubated with H$_2$O or 3, 10, or 30 μM Trx+0.1 μM TR and 2 mM NADPH for 20 minutes and log G* was determined by magnetic microrheometry. Data is presented as the difference in log G* measurements recorded before and after exposure (displayed on the Y-axis). Each column represents the mean±standard error for 4 samples (♦Statistically significant from H₂O diluent value). Incubation of sputum with diluent (H₂O) for 20 minutes, resulted in a modest decline in log G* (0.11 log units) compared with pretreatment values. Exposure to Trx (3 µM), TR (0.1 µM) and NADPH (2 mM) resulted in a significant decrease in the log G* (0.26 log units) compared to diluent treatment alone (FIG. 4A). More substantial declines were evident in samples exposed to higher concentrations of Trx (0.39 log units decreased at 10 µM Trx and 0.65 log units decreased at 30 µM Trx, respectively).

The effect of varying concentrations of NADPH was also examined (FIG. 4B; change in log G* after incubation with H₂O or 10 µM Trx, 0.1 µM TR, and 0.2, 0.6 or 2 mM NADPH). Sputum exposed to Trx (30 µM), TR (0.1 µM) and a low concentration of NADPH (0.2 mM) exhibited a modest decline in viscoelasticity (0.16 log units). A further decline in viscoelasticity occurred with exposure to higher NADPH concentrations, 0.6 mM (0.26 log units) and 2 mM (0.39 log units), demonstrating the importance of provision of reducing equivalents to allow Trx-mediated reduction in sputum viscoelasticity.

Example 5

The following example describes the effect of Trx on the solubility of sputum glycoproteins.

Figure 5:
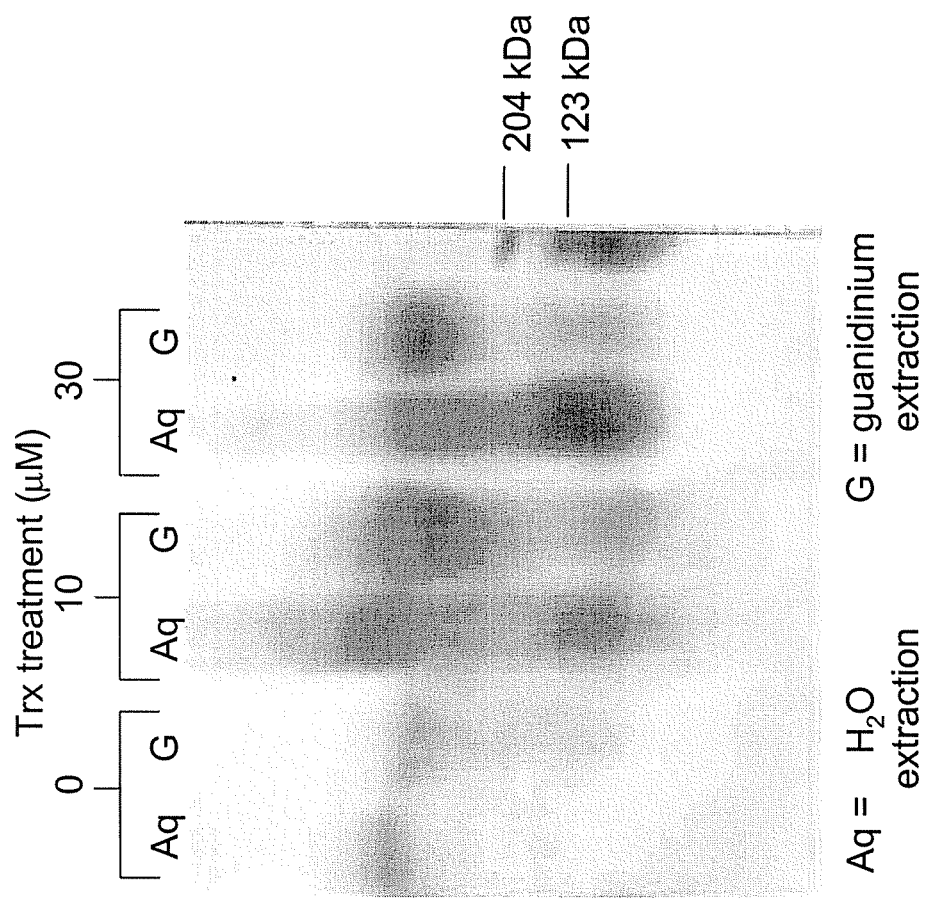
FIG. 5 is a digitized image showing the glycoprotein mass profile of CF sputum after diluent or Trx exposure.

Disulfide bonds on mucin glycoprotein polymers are potential targets for reduction by Trx. To examine the effect of Trx on glycoproteins present in sputum, aliquots of sputum were incubated with H₂O, 10 or 30 µM Trx with its reducing system for 20 minutes and separated into aqueous (Aq) and gel fractions by centrifugation. Each insoluble gel fraction was further treated for 14 hours with guanidinium (G). After treatment, the resulting soluble and insoluble phases of each sample were separated and analyzed for glycoprotein content by periodic acid/Schiff reagent (PAS) staining Specifically, fractions were loaded and electrophoresed in a 1% agarose (w/v) gel, transferred to PVDF membrane, and stained with periodic acid/Schiff reagent as described in materials and methods. Referring to FIG. 5, molecular weight standards are shown in far right lane. Results are representative of three independent experiments.

As shown in FIG. 5, a discrete population of high molecular weight glycoproteins was detected in both the soluble and gel fractions derived from sputum treated with diluent. In contrast, greater amounts of PAS-reactive glycoproteins were evident in both phases derived from sputum treated with 10 or 30 µM Trx. During the processing of these samples, it was observed that the gel phase matrix from diluent treated samples retained a high degree of insolubility, despite overnight guanidinium treatment. This insolubility is the likely reason for the quantitative difference in amounts of glycoprotein observed in gel phase lanes from diluent and Trx-treated sputum. In addition to being more abundant, a substantial proportion of the glycoforms in Trx-exposed samples also exhibited greater electrophoretic mobility than those moieties present in diluent-treated samples. These findings indicate that Trx increases the solubility, and reduces the size of glycoprotein polymers in sputum.

Example 6

The following example demonstrates the effect of Trx on the solubility of DNA in sputum.

Figure 6:
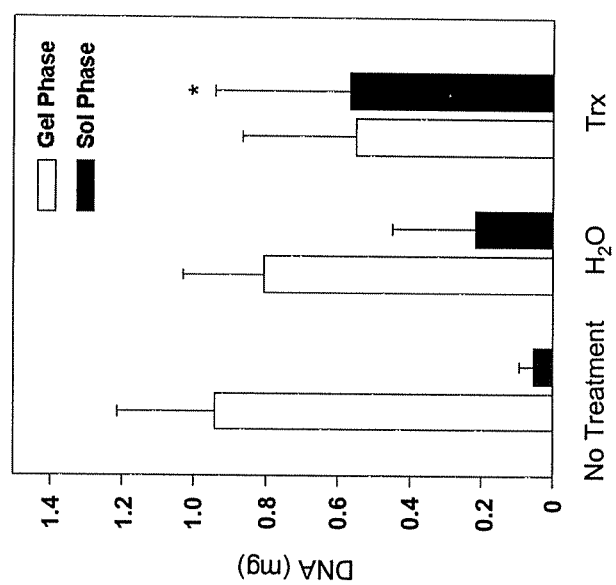
FIG. 6 is a graph showing that Trx exposure increases the solubility of DNA present in CF sputum.

The presence of high amounts of extracellular DNA in CF airway secretions contributes to the excessive viscoelasticity of CF sputum. To evaluate what effect Trx has on the solubility of DNA in sputum, sputum samples (275 µl) were incubated with either no additions, diluent (H₂O), or Trx (30 µM)+reducing system for 20 minutes, and then separated into gel (insoluble) and liquid (soluble) phases. Measurement of DNA content by Hoechst assay revealed that most of the DNA present in the untreated samples was retained in the gel phase (gel=0.94±0.26 mg; liquid=0.05±0.03 mg) (FIG. 6). Diluent-treated samples demonstrated a modest increase in mean DNA content in their liquid phase (gel=0.80±0.24 mg; liquid=0.21±0.23 mg). With Trx treatment, a further shift in DNA from gel to liquid phase (gel=0.55±0.31 mg; liquid=0.57±0.37 mg) was observed. Referring to FIG. 6, shown are mean DNA content±S.D. from each fraction (n=5 experiments) (*P<0.05 versus no treatment soluble phase).

Example 7

The following example describes the treatment of a patient that has excessively viscous or cohesive mucus or sputum with the therapeutic composition of the invention.

A 4 month old female patient presents with poor weight; frequent, bulky, foul-smelling, oily stools; a protruding abdomen and recurrent coughing and wheezing. The patient undergoes a quantitative pilocarpine iontophoresis sweat test and is diagnosed with cystic fibrosis. Pulmonary function tests and a chest X-ray confirm the diagnosis. The patient undergoes periodic evaluation and therapy including prevention and treatment of lung problems as they occur, good nutrition, and physical activity. By age 13, the patient displays slowed growth, delayed puberty, and declining physical endurance, and frequently suffers from lung infections, labored breathing and gastrointestinal discomfort. The patient presents at the physician's office with a severe cough, wheezing and impaired lung function.

A compaction assay is performed on a sample of sputum collected from the airway of the patient and it is determined based on this assay and the prior diagnosis of cystic fibrosis that the patient is suffering from respiratory dysfunction due to excessively viscous and cohesive mucus in the airways. To treat this symptom in the lung, the patient is administered a composition comprising about 2.5 mg per dosing unit of human thioredoxin and a dose of NAPDH sufficient to achieve about 5 µM achieved surface concentration in a surfactant by aerosol delivery. The patient is monitored subsequently by additional compaction assays for increased liquefaction of the sputum and by lung function testing for clearing of the airways. Subsequent doses of the composition as described above are administered by aerosol on a daily basis until the patient airways show a significant clearance and the patient symptoms and general health have improved.

Each of the publications and other references discussed or cited herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of treating abnormal or excessively viscous or cohesive mucus or sputum in a patient, comprising contacting the mucus or sputum of the patient with a composition comprising a thioredoxin protein or peptide having an amino acid sequence that is at least 80% identical to SEQ ID NO:12 and having protein disulfide reductase activity.

2. The method of claim 1, wherein the thioredoxin protein or peptide having an amino acid sequence that is at least 85% identical to SEQ ID NO:12.

3. The method of claim 1, wherein the thioredoxin protein or peptide having an amino acid sequence that is at least 90% identical to SEQ ID NO:12.

4. The method of claim 1, wherein the thioredoxin protein or peptide having an amino acid sequence that is at least 95% identical to SEQ ID NO:12.

5. The method of claim 1, wherein the thioredoxin protein or peptide having an amino acid sequence that is at least 98% identical to SEQ ID NO:12.

6. The method of claim 1, wherein the patient has a lung disease in which abnormal or excessive viscosity or cohesiveness of mucus or sputum is a symptom or cause of the disease.

7. The method of claim 1, wherein the patient has cystic fibrosis.

8. The method of claim 1, wherein the step of contacting the mucus or sputum of the patient with the composition is performed by introducing the composition to the patient by a route selected from the group consisting of nasal, intratracheal, bronchial, direct installation into the lung and inhaled.

9. The method of claim 8, wherein the step of contacting the mucus or sputum of the patient with the composition is performed by introducing the composition to the patient by inhalation.

10. The method of claim 1, wherein the mucus or sputum to be contacted is located in the respiratory tract, the gastrointestinal tract or the reproductive tract of the patient.

11. The method of claim 1, wherein the composition is administered to the patient in a pharmaceutically acceptable carrier.

12. The method of claim 1, wherein the protein or peptide is administered to the patient in an amount that is between about 1.5 mmoles/kg weight of the patient and about 150 mmoles/kg weight of the patient.

13. The method of claim 1, wherein the protein has a half-life in the patient of between about 5 minutes and about 24 hours.

14. The method of claim 1, wherein the protein comprises human thioredoxin.

15. The method of claim 1, wherein the composition further comprises at least one additional agent for treatment of excessively viscous or cohesive mucus or sputum.

16. A method of treating abnormal or excessively viscous or cohesive mucus or sputum in a patient having cystic fibrosis, comprising contacting the mucus or sputum of the patient with a composition comprising a thioredoxin protein or peptide having peptide having an amino acid sequence that is at least 80% identical to SEQ ID NO:12 and having protein disulfide reductase activity.

17. A method of treating abnormal or excessively viscous or cohesive mucus or sputum in a patient having cystic fibrosis, comprising contacting the mucus or sputum of the patient with a composition comprising a thioredoxin protein or peptide peptide having an amino acid sequence that is at least 80% identical to SEQ ID NO:12 and having protein disulfide reductase activity and wherein the step of contacting the mucus or sputum of the patient with the composition is performed by introducing the composition to the patient by inhalation.

* * * * *

SEQUENCE LISTING

<160> NUMBER OF SEQ ID NOS: 15

<210> SEQ ID NO 1
<211> LENGTH: 4
<212> TYPE: PRT
<213> ORGANISM: Artificial sequence
<220> FEATURE:
<223> OTHER INFORMATION: synthetic peptide motif

<400> SEQUENCE: 1

Cys Gly Pro Cys
1

<210> SEQ ID NO 2
<211> LENGTH: 6
<212> TYPE: PRT
<213> ORGANISM: Artificial sequence
<220> FEATURE:
<223> OTHER INFORMATION: synthetic peptide motif
<220> FEATURE:
<221> NAME/KEY: misc_feature
<222> LOCATION: (1)..(6)
<223> OTHER INFORMATION: Xaa = any amino acid

<400> SEQUENCE: 2

Xaa Cys Gly Pro Cys Xaa
1               5

<210> SEQ ID NO 3
<211> LENGTH: 6
<212> TYPE: PRT
<213> ORGANISM: Artificial sequence
<220> FEATURE:
<223> OTHER INFORMATION: synthetic peptide motif

<400> SEQUENCE: 3

Trp Cys Gly Pro Cys Lys
1               5

<210> SEQ ID NO 4
<211> LENGTH: 109
<212> TYPE: PRT
<213> ORGANISM: Pseudomonas syringae

<400> SEQUENCE: 4

Met Ser Asn Asp Leu Ile Lys His Val Thr Asp Ala Ser Phe Glu Ala
1               5                   10                  15

Asp Val Leu Lys Ala Asp Gly Ala Val Leu Val Asp Tyr Trp Ala Glu
            20                  25                  30

Trp Cys Gly Pro Cys Lys Met Ile Ala Pro Val Leu Asp Glu Ile Ala
        35                  40                  45

Thr Thr Tyr Ala Gly Lys Leu Thr Ile Ala Lys Leu Asn Ile Asp Glu
    50                  55                  60

Asn Gln Glu Thr Pro Ala Lys His Gly Val Arg Gly Ile Pro Thr Leu
65                  70                  75                  80

Met Leu Phe Lys Asn Gly Asn Val Glu Ala Thr Lys Val Gly Ala Leu
                85                  90                  95

Ser Lys Ser Gln Leu Ala Ala Phe Leu Asp Ala Asn Ile
            100                 105

<210> SEQ ID NO 5
<211> LENGTH: 104
<212> TYPE: PRT

<213> ORGANISM: Porphyromonas gingivalis

<400> SEQUENCE: 5

Met Ala Leu Gln Ile Thr Asp Ala Thr Phe Asp Gly Leu Val Ala Glu
1               5                   10                  15

Gly Lys Pro Met Val Val Asp Phe Trp Ala Thr Trp Cys Gly Pro Cys
            20                  25                  30

Arg Met Val Gly Pro Ile Ile Asp Glu Leu Ala Ala Glu Tyr Glu Gly
        35                  40                  45

Arg Ala Ile Ile Gly Lys Val Asp Val Asp Ala Asn Thr Glu Leu Pro
    50                  55                  60

Met Lys Tyr Gly Val Arg Asn Ile Pro Thr Ile Leu Phe Ile Lys Asn
65                  70                  75                  80

Gly Glu Val Val Lys Lys Leu Val Gly Ala Gln Ser Lys Asp Val Phe
                85                  90                  95

Lys Lys Glu Leu Asp Ala Leu Phe
            100

<210> SEQ ID NO 6
<211> LENGTH: 103
<212> TYPE: PRT
<213> ORGANISM: Listeria monocytogenes

<400> SEQUENCE: 6

Met Val Lys Glu Ile Thr Asp Ala Thr Phe Glu Gln Glu Thr Ser Glu
1               5                   10                  15

Gly Leu Val Leu Thr Asp Phe Trp Ala Thr Trp Cys Gly Pro Cys Arg
            20                  25                  30

Met Val Ala Pro Val Leu Glu Glu Ile Gln Glu Glu Arg Gly Glu Ala
        35                  40                  45

Leu Lys Ile Val Lys Met Asp Val Asp Glu Asn Pro Glu Thr Pro Gly
    50                  55                  60

Ser Phe Gly Val Met Ser Ile Pro Thr Leu Leu Ile Lys Lys Asp Gly
65                  70                  75                  80

Glu Val Val Glu Thr Ile Ile Gly Tyr Arg Pro Lys Glu Glu Leu Asp
                85                  90                  95

Glu Val Ile Asn Lys Tyr Val
            100

<210> SEQ ID NO 7
<211> LENGTH: 103
<212> TYPE: PRT
<213> ORGANISM: Saccharomyces cerevisiae

<400> SEQUENCE: 7

Met Val Thr Gln Phe Lys Thr Ala Ser Glu Phe Asp Ser Ala Ile Ala
1               5                   10                  15

Gln Asp Lys Leu Val Val Val Asp Phe Tyr Ala Thr Trp Cys Gly Pro
            20                  25                  30

Cys Lys Met Ile Ala Pro Met Ile Glu Lys Phe Ser Glu Gln Tyr Pro
        35                  40                  45

Gln Ala Asp Phe Tyr Lys Leu Asp Val Asp Glu Leu Gly Asp Val Ala
    50                  55                  60

Gln Lys Asn Glu Val Ser Ala Met Pro Thr Leu Leu Leu Phe Lys Asn
65                  70                  75                  80

Gly Lys Glu Val Ala Lys Val Val Gly Ala Asn Pro Ala Ala Ile Lys
                85                  90                  95

```
Gln Ala Ile Ala Ala Asn Ala
            100

<210> SEQ ID NO 8
<211> LENGTH: 105
<212> TYPE: PRT
<213> ORGANISM: Gallus gallus

<400> SEQUENCE: 8

Met Val Lys Ser Val Gly Asn Leu Ala Asp Phe Glu Ala Glu Leu Lys
1               5                   10                  15

Ala Ala Gly Glu Lys Leu Val Val Asp Phe Ser Ala Thr Trp Cys
            20                  25                  30

Gly Pro Cys Lys Met Ile Lys Pro Phe Phe His Ser Leu Cys Asp Lys
            35                  40                  45

Phe Gly Asp Val Val Phe Ile Glu Ile Asp Val Asp Asp Ala Gln Asp
    50                  55                  60

Val Ala Thr His Cys Asp Val Cys Met Pro Thr Phe Gln Phe Tyr
65                  70                  75                  80

Lys Asn Gly Lys Lys Val Gln Glu Phe Ser Gly Ala Asn Lys Glu Lys
                85                  90                  95

Leu Glu Glu Thr Ile Lys Ser Leu Val
            100                 105

<210> SEQ ID NO 9
<211> LENGTH: 105
<212> TYPE: PRT
<213> ORGANISM: Mus musculus

<400> SEQUENCE: 9

Met Val Lys Leu Ile Glu Ser Lys Glu Ala Phe Gln Glu Ala Leu Ala
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Cys Asp Lys
            35                  40                  45

Tyr Ser Asn Val Val Phe Leu Glu Val Asp Val Asp Asp Cys Gln Asp
    50                  55                  60

Val Ala Ala Asp Cys Glu Val Cys Met Pro Thr Phe Gln Phe Tyr
65                  70                  75                  80

Lys Lys Gly Gln Lys Val Gly Glu Phe Ser Gly Ala Asn Lys Glu Lys
                85                  90                  95

Leu Glu Ala Ser Ile Thr Glu Tyr Ala
            100                 105

<210> SEQ ID NO 10
<211> LENGTH: 105
<212> TYPE: PRT
<213> ORGANISM: Rattus norvegicus

<400> SEQUENCE: 10

Met Val Lys Leu Ile Glu Ser Lys Glu Ala Phe Gln Glu Ala Leu Ala
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Cys Asp Lys
            35                  40                  45

Tyr Ser Asn Val Val Phe Leu Glu Val Asp Val Asp Asp Cys Gln Asp
    50                  55                  60
```

```
Val Ala Ala Asp Cys Glu Val Lys Cys Met Pro Thr Phe Gln Phe Tyr
 65                  70                  75                  80

Lys Lys Gly Gln Lys Val Gly Glu Phe Ser Gly Ala Asn Lys Glu Lys
                 85                  90                  95

Leu Glu Ala Thr Ile Thr Glu Phe Ala
                100                 105

<210> SEQ ID NO 11
<211> LENGTH: 105
<212> TYPE: PRT
<213> ORGANISM: Bos taurus

<400> SEQUENCE: 11

Met Val Lys Gln Ile Glu Ser Lys Tyr Ala Phe Gln Glu Ala Leu Asn
1               5                   10                  15

Ser Ala Gly Glu Lys Leu Val Val Asp Phe Ser Ala Thr Trp Cys
                 20                  25                  30

Gly Pro Cys Lys Met Ile Lys Pro Phe Phe His Ser Leu Ser Glu Lys
             35                  40                  45

Tyr Ser Asn Val Val Phe Leu Glu Val Asp Val Asp Asp Cys Gln Asp
         50                  55                  60

Val Ala Ala Glu Cys Glu Val Lys Cys Met Pro Thr Phe Gln Phe Phe
 65                  70                  75                  80

Lys Lys Gly Gln Lys Val Gly Glu Phe Ser Gly Ala Asn Lys Glu Lys
                 85                  90                  95

Leu Glu Ala Thr Ile Asn Glu Leu Ile
                100                 105

<210> SEQ ID NO 12
<211> LENGTH: 105
<212> TYPE: PRT
<213> ORGANISM: Homo sapiens

<400> SEQUENCE: 12

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
                 20                  25                  30

Gly Pro Cys Lys Met Ile Lys Pro Phe Phe His Ser Leu Ser Glu Lys
             35                  40                  45

Tyr Ser Asn Val Ile Phe Leu Glu Val Asp Val Asp Asp Cys Gln Asp
         50                  55                  60

Val Ala Ser Glu Cys Glu Val Lys Cys Met Pro Thr Phe Gln Phe Phe
 65                  70                  75                  80

Lys Lys Gly Gln Lys Val Gly Glu Phe Ser Gly Ala Asn Lys Glu Lys
                 85                  90                  95

Leu Glu Ala Thr Ile Asn Glu Leu Val
                100                 105

<210> SEQ ID NO 13
<211> LENGTH: 134
<212> TYPE: PRT
<213> ORGANISM: Arabidopsis thaliana

<400> SEQUENCE: 13

Met Gly Gly Ala Leu Ser Thr Val Phe Gly Ser Gly Glu Asp Ala Ala
1               5                   10                  15

Ala Ala Gly Thr Glu Ser Ser Glu Pro Ser Arg Val Leu Lys Phe Ser
```

```
                    20                  25                  30
Ser Ser Ala Arg Trp Gln Leu His Phe Asn Glu Ile Lys Glu Ser Asn
        35                  40                  45

Lys Leu Leu Val Val Asp Phe Ser Ala Ser Trp Cys Gly Pro Cys Arg
        50                  55                  60

Met Ile Glu Pro Ala Ile His Ala Met Ala Asp Lys Phe Asn Asp Val
65                  70                  75                  80

Asp Phe Val Lys Leu Asp Val Asp Glu Leu Pro Asp Val Ala Lys Glu
                85                  90                  95

Phe Asn Val Thr Ala Met Pro Thr Phe Val Leu Val Lys Arg Gly Lys
                100                 105                 110

Glu Ile Glu Arg Ile Ile Gly Ala Lys Lys Asp Glu Leu Glu Lys Lys
            115                 120                 125

Val Ser Lys Leu Arg Ala
        130

<210> SEQ ID NO 14
<211> LENGTH: 167
<212> TYPE: PRT
<213> ORGANISM: Zea mays

<400> SEQUENCE: 14

Met Ala Met Glu Thr Cys Phe Arg Ala Trp Ala Leu His Ala Pro Ala
1               5                   10                  15

Gly Ser Lys Asp Arg Leu Leu Val Gly Asn Leu Val Leu Pro Ser Lys
                20                  25                  30

Arg Ala Leu Ala Pro Leu Ser Val Gly Arg Val Ala Thr Arg Arg Pro
        35                  40                  45

Arg His Val Cys Gln Ser Lys Asn Ala Val Asp Glu Val Val Val Ala
        50                  55                  60

Asp Glu Lys Asn Trp Asp Gly Leu Val Met Ala Cys Glu Thr Pro Val
65                  70                  75                  80

Leu Val Glu Phe Trp Ala Pro Trp Cys Gly Pro Cys Arg Met Ile Ala
                85                  90                  95

Pro Val Ile Asp Glu Leu Ala Lys Asp Tyr Ala Gly Lys Ile Thr Cys
                100                 105                 110

Cys Lys Val Asn Thr Asp Asp Ser Pro Asn Val Ala Ser Thr Tyr Gly
                115                 120                 125

Ile Arg Ser Ile Pro Thr Val Leu Ile Phe Lys Gly Gly Glu Lys Lys
            130                 135                 140

Glu Ser Val Ile Gly Ala Val Pro Lys Ser Thr Leu Thr Thr Leu Ile
145                 150                 155                 160

Asp Lys Tyr Ile Gly Ser Ser
                165

<210> SEQ ID NO 15
<211> LENGTH: 172
<212> TYPE: PRT
<213> ORGANISM: Oryza sativa

<400> SEQUENCE: 15

Met Ala Leu Glu Thr Cys Phe Arg Ala Trp Ala Thr Leu His Ala Pro
1               5                   10                  15

Gln Pro Pro Ser Ser Gly Gly Ser Arg Asp Arg Leu Leu Leu Ser Gly
                20                  25                  30

Ala Gly Ser Ser Gln Ser Lys Pro Arg Leu Ser Val Ala Ser Pro Ser
        35                  40                  45
```

-continued

```
Pro Leu Arg Pro Ala Ser Arg Phe Ala Cys Gln Cys Ser Asn Val Val
    50                  55                  60
Asp Glu Val Val Ala Asp Glu Lys Asn Trp Asp Ser Met Val Leu
65              70                  75                  80
Gly Ser Glu Ala Pro Val Leu Val Glu Phe Trp Ala Pro Trp Cys Gly
                85                  90                  95
Pro Cys Arg Met Ile Ala Pro Val Ile Asp Glu Leu Ala Lys Glu Tyr
            100             105                 110
Val Gly Lys Ile Lys Cys Cys Lys Val Asn Thr Asp Asp Ser Pro Asn
        115             120                 125
Ile Ala Thr Asn Tyr Gly Ile Arg Ser Ile Pro Thr Val Leu Met Phe
    130             135                 140
Lys Asn Gly Glu Lys Lys Glu Ser Val Ile Gly Ala Val Pro Lys Thr
145             150                 155                 160
Thr Leu Ala Thr Ile Ile Asp Lys Tyr Val Ser Ser
            165             170
```